United States Patent
Shapiro

(10) Patent No.: US 9,395,880 B2
(45) Date of Patent: Jul. 19, 2016

(54) HEALTH INFORMATION MAPPING SYSTEM WITH GRAPHICAL EDITOR

(75) Inventor: Samuel W. Shapiro, Kaysville, UT (US)

(73) Assignee: QVERA LLC, Kaysville, UT (US)

( * ) Notice: Subject to any disclaimer, the term of this patent is extended or adjusted under 35 U.S.C. 154(b) by 544 days.

(21) Appl. No.: 13/494,270

(22) Filed: Jun. 12, 2012

(65) Prior Publication Data

US 2013/0332873 A1   Dec. 12, 2013

(51) Int. Cl.
| | |
|---|---|
| *G06Q 50/22* | (2012.01) |
| *G06F 3/0482* | (2013.01) |
| *G06F 9/44* | (2006.01) |
| *G06F 3/0484* | (2013.01) |

(52) U.S. Cl.
CPC ............ *G06F 3/0482* (2013.01); *G06F 3/0484* (2013.01); *G06F 8/34* (2013.01)

(58) Field of Classification Search
CPC .................................. G06F 8/34; G06Q 50/22
USPC ............................................... 715/771; 705/2
See application file for complete search history.

(56) References Cited

U.S. PATENT DOCUMENTS

| | | | | |
|---|---|---|---|---|
| 6,725,447 | B1 * | 4/2004 | Gilman et al. ................. | 717/105 |
| 7,483,924 | B2 * | 1/2009 | Cohen et al. | |
| 7,512,633 | B2 * | 3/2009 | Cohen et al. | |
| 7,810,164 | B2 * | 10/2010 | Hiroi et al. ...................... | 726/28 |
| 7,890,517 | B2 * | 2/2011 | Angelo et al. ................. | 707/752 |
| 8,306,831 | B2 * | 11/2012 | Eisenberger et al. ............ | 705/3 |
| 2003/0088438 | A1 * | 5/2003 | Maughan et al. ................. | 705/2 |
| 2005/0256380 | A1 * | 11/2005 | Nourie et al. ................. | 600/300 |
| 2005/0273367 | A1 * | 12/2005 | Nourie et al. ..................... | 705/3 |
| 2006/0080386 | A1 * | 4/2006 | Roykkee et al. .............. | 709/203 |
| 2006/0161840 | A1 * | 7/2006 | Cohen et al. ................... | 715/513 |
| 2006/0206361 | A1 * | 9/2006 | Logan .............................. | 705/3 |
| 2006/0206523 | A1 * | 9/2006 | Gaurav et al. .............. | 707/104.1 |
| 2007/0016610 | A1 * | 1/2007 | Cohen et al. .............. | 707/104.1 |
| 2007/0299688 | A1 * | 12/2007 | Braz et al. ......................... | 705/2 |
| 2008/0046292 | A1 * | 2/2008 | Myers et al. ..................... | 705/3 |
| 2008/0082379 | A1 * | 4/2008 | Patterson et al. ................ | 705/7 |
| 2008/0255885 | A1 * | 10/2008 | Eisenberger et al. ............. | 705/3 |

(Continued)

OTHER PUBLICATIONS

Screenshot of Qvera Interface Engine manufactured by Qvera, Wayback Machine, available at <http://web.archive.org>, archived on Jan 27, 2012, 10 pages.*

*Primary Examiner* — Reza Nabi
(74) *Attorney, Agent, or Firm* — Durham Jones & Pinegar, P.C. Intellectual Property Law Group

(57) ABSTRACT

A mapping system provides a graphical editor, consisting of a visual channel editor and a node configuration panel, for graphically defining channels for processing messages. Within the visual channel editor, the user is able to create a graphical representation of a channel by interconnecting representations of a source node, mapping nodes, condition nodes, and destination nodes. When a node is selected in the visual channel editor, the node configuration panel displays user interface controls in which the user specifies parameters for the selected node. The mapping system automatically generates scripts for implementing the functionality defined by the user input. In this manner, a user need not have any knowledge of scripting to define mappings to apply to messages. The mapping system may be used to perform mappings of messages of virtually any type, but has specific applicability to mapping messages between Health Information Technology (HIT) systems.

16 Claims, 24 Drawing Sheets

(56) References Cited

U.S. PATENT DOCUMENTS

| | | | |
|---|---|---|---|
| 2008/0288294 A1* | 11/2008 | Eisenberger et al. | 705/3 |
| 2010/0088117 A1* | 4/2010 | Belden et al. | 705/3 |
| 2010/0256994 A1* | 10/2010 | Eisenberger et al. | 705/3 |
| 2011/0093519 A1* | 4/2011 | Carricarte et al. | 709/203 |
| 2011/0231203 A1* | 9/2011 | Rosow et al. | 705/2 |
| 2012/0200507 A1* | 8/2012 | Flam et al. | 345/173 |
| 2012/0203566 A1* | 8/2012 | Kidd et al. | 705/2 |
| 2012/0284734 A1* | 11/2012 | Mcquaid et al. | 719/321 |
| 2013/0173281 A1* | 7/2013 | Rosow et al. | 705/2 |
| 2013/0185094 A1* | 7/2013 | Mukerji et al. | 705/3 |
| 2013/0218917 A1* | 8/2013 | Bell | 707/756 |
| 2013/0304510 A1* | 11/2013 | Chen et al. | 705/3 |
| 2013/0325512 A1* | 12/2013 | Kim et al. | 705/3 |
| 2014/0052779 A1* | 2/2014 | Britton et al. | 709/203 |
| 2014/0119632 A1* | 5/2014 | Yuz et al. | 382/132 |
| 2014/0122734 A1* | 5/2014 | Higgins et al. | 709/231 |
| 2014/0164564 A1* | 6/2014 | Hoofnagle et al. | 709/217 |

* cited by examiner

HEALTH INFORMATION MAPPING SYSTEM WITH GRAPHICAL EDITOR

BACKGROUND

Health information technology (HIT) refers to the digitization of health information. Many HIT systems exist which use electronic health records instead of paper medical records to store patients' health information. The use of electronic health records has facilitated the portability of health information. However, many significant drawbacks exist when using existing HIT systems.

A primary drawback of current HIT systems is the lack of interoperability between different systems. For example, many different formats exist for storing and exchanging health information digitally, including HL7, XML, and CSV among others. Even when a common format is used between two systems, the use of different schemas may still prevent two systems from directly interoperating.

To address this interoperability issue, tools have been created that perform mappings between formats. These tools allow an administrator to define mappings to apply to source data to convert the source data from one format to another or from one schema to another. For example, if the source data comes from a HIT system that stores data in the HL7 format, such tools can be used to apply mappings to the source data to convert it into the XML format for use by a HIT system that stores data in the XML format.

To create mappings in current tools, however, the administrator is required to write scripts, something that is not within the toolset of many potential users of such tools. For example, most health care providers need to provide some form of interoperability between their HIT system and other HIT systems. Many of these health care providers, such as smaller clinics, may not have the personnel on staff, or the financial means, to employ an administrator with scripting skills sufficient to create such mappings.

Even if a health care provider has the ability to create mappings to provide interoperability with its HIT system, the process of writing scripts to perform such mappings is a tedious and error prone process. For these reasons, the portability of health information has not reached the levels desired by the health care industry.

BRIEF SUMMARY

This application discloses embodiments of methods, systems, and computer program products for facilitating the creation of channels for mapping messages of health information systems from one format to another. This application may provide embodiments of a mapping system that may include a graphical editor, consisting of a visual channel editor and a node configuration panel, for graphically defining channels.

Within the visual channel editor, the user may be able to create a graphical representation of a channel by interconnecting graphical representations of a source node, zero or more mapping nodes, zero or more condition nodes, and one or more destination nodes. When a node is selected in the visual channel editor, the node configuration panel may display user interface controls in which the user specifies parameters for the selected node. Various predefined types for each type of node can be provided for user selection. Depending on which predefined type is selected, appropriate user interface controls can be displayed to receive the necessary input to configure the corresponding node appropriately.

If a user graphically creates a channel and specifies the appropriate parameters for each node, the mapping system may automatically generate scripts for implementing the functionality defined by the user input to the user interface controls. In this manner, the user can graphically create channels for mapping messages including mapping messages of an HIT system to another format to allow for the intercommunication of disparate HIT systems. By allowing the graphical creation of channels, the mapping system may provide many more users, including those without any knowledge of scripting, with the tools to perform mapping of messages.

In some embodiments, a visual channel editor can be displayed on a display device. Graphical representations of channel nodes can be arranged and interconnected to define a channel within the visual channel editor. The graphical representations can include a graphical representation of a source node, a graphical representation of zero or more mapping nodes, a graphical representation of zero or more condition nodes, and at least one graphical representation of a destination node.

User input can be received that selects one of the graphical representations. The selected graphical representation corresponds to a first channel node. In response to the selection of the graphical representation, a node configuration panel can be displayed. The node configuration panel displays one or more user interface controls that the user can manipulate to define configurable parameters for the first channel node.

User input can be received to the one or more user interface controls. The user input defines configurable parameters for the first channel node. The user input to the one or more user interface controls can be used to automatically generate one or more scripts to implement functionality specified in the defined configurable parameters on messages that are processed by the first channel node.

Additional features and advantages will be set forth in the description which follows, and in part will be obvious from the description, or may be learned by the practice of the methods and systems disclosed herein. The features and advantages of the methods and systems may be realized and obtained by using the instruments and combinations particularly pointed out in the claims. These and other features will become more fully apparent from the following description and appended claims, or may be learned by the practice of the methods and systems as set forth hereinafter.

BRIEF DESCRIPTION OF THE DRAWINGS

In order to describe the manner in which the above-recited and other features of the described methods and systems can be obtained, a more particular description of embodiments briefly described above will be rendered by reference to the appended drawings. These drawings depict only some exemplary embodiments and are not therefore to be considered to be limiting in scope, which is only limited by the appended claims. The methods and systems will be described and explained with additional specificity and detail through the use of the accompanying drawings in which:

Figure 1:
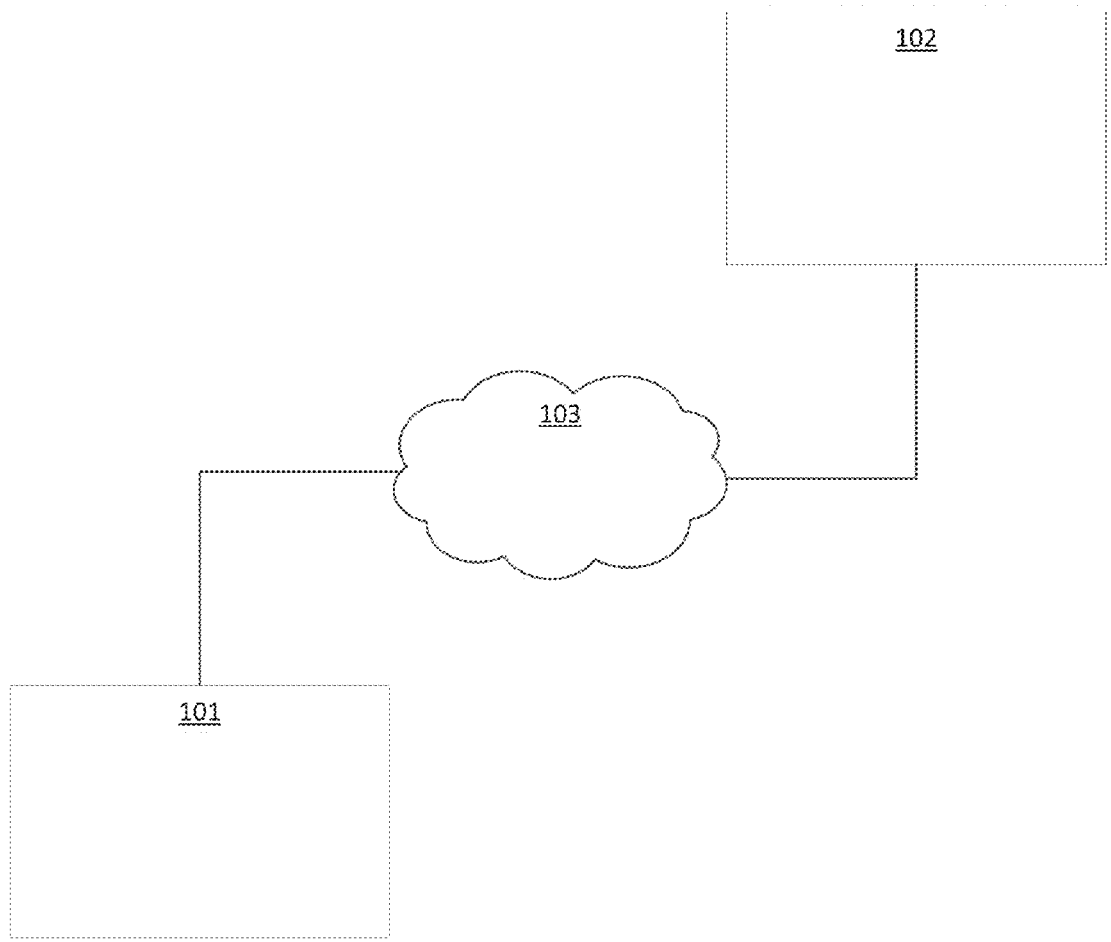
FIG. 1 illustrates an exemplary computer system in which health information mapping systems can be implemented.

The Figures illustrate specific aspects of exemplary systems and methods as described below. Together with the following description, the Figures demonstrate and explain the principles of the elements, components, structures, methods, and principles described herein. In the drawings, various components may be exaggerated, simplified, or otherwise modified for clarity. The same reference numerals in different drawings represent the same element and/or component, and thus their descriptions will not be repeated. Furthermore, well-known method steps, components, materials, or operations are not shown or described in detail to avoid obscuring aspects of the described devices. Moreover, the Figures may show simplified or partial views, and the dimensions and physical representations of elements in the Figures may be exaggerated or otherwise not in proportion for clarity.

DETAILED DESCRIPTION

The following description supplies specific details in order to provide a thorough understanding. Nevertheless, the skilled artisan would understand that the described health information mapping systems and methods of creating and using the health information mapping systems and methods can be implemented and used without employing these specific details. Indeed, the methods and systems can be placed into practice by modifying the illustrated components and methods and can be used in conjunction with any other apparatus and techniques conventionally used in the industry.

Embodiments of health information mapping tools, systems, and/or methods may include or utilize a special purpose or general-purpose computer including computer hardware, such as, for example, one or more processors and system memory, as discussed in greater detail below. Embodiments may also include physical and other computer-readable media for carrying or storing computer-executable instructions and/or data structures. Such computer-readable media can be any available media that can be accessed by a general purpose or special purpose computer system. Computer-readable media that store computer-executable instructions may be computer storage media (devices). Computer-readable media that carry computer-executable instructions may be transmission media. Thus, by way of example, and not limitation, embodiments can include at least two distinctly different kinds of computer-readable media: computer storage media (devices) and transmission media.

Computer storage media (devices) may include RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" may be defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer may properly view the connection as a transmission medium. Transmissions media can include a network and/or data links which can be used to carry desired program code elements in the form of computer-executable instructions or data structures and which can be accessed by a general purpose or special purpose computer. Combinations of the above may also be included within the scope of computer-readable media.

Further, upon reaching various computer system components, program code elements in the form of computer-executable instructions or data structures can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. Thus, it should be understood that computer storage media (devices) can be included in computer system components that also (or even primarily) utilize transmission media.

Computer-executable instructions may include, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it may also be understood that the subject matter defined in the appended claims is not necessarily limited to the described features or acts described above. Rather, the described features and acts are disclosed as example forms of implementing the claims.

Described embodiments may be practiced in network computing environments with many types of computer system configurations, including, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, and the like. Described embodiments may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Exemplary Embodiment of a Computer Environment

FIG. 1 illustrates an exemplary embodiment of computer environment 100 in which the present invention can be implemented. Computer environment 100 may represent a general environment for ease of illustration; however, computer environment 100 can be used in virtually any computer system having any type, or no, network connectivity.

Computer environment 100 may also include computer system 101, database 102 accessible by computer system 101, and network 103 to which computer system 101 may be connected. In a basic configuration, computer system 101 can represent a server or other computer system located in a clinic, hospital, or other health care provider location, database 102 can be a local or remotely stored database, and network 103 can be the internet or an intranet. Of course, more complex configurations can exist such as when computer system 101 and/or database 102 represent resources in a cloud of computer systems, or other similar configurations.

Computer system 101 can include a display on which the graphical editor of the present invention can be displayed to allow a user to create channels for mapping data from a source (e.g., from database 102 or any other local or remote source) to one or more destinations (e.g., to database 102 or any other local or remote destination). Once created, these channels can be stored on computer system 101 or at any other accessible location.

In this description, the unit of data that a channel operates on can be referred to as a message. A message can be viewed as synonymous with a file in most instances. Some examples of messages may include an HL7 message, a CSV file, an XML file, etc. Mapping a message can refer to the processing of a message through a channel. Accordingly, mapping may include not only applying modifications to data of a message, but also applying conditions to the data of a message, and filtering or relocating a message based on the data of the message.

Visual Channel Editor

Figure 2A:
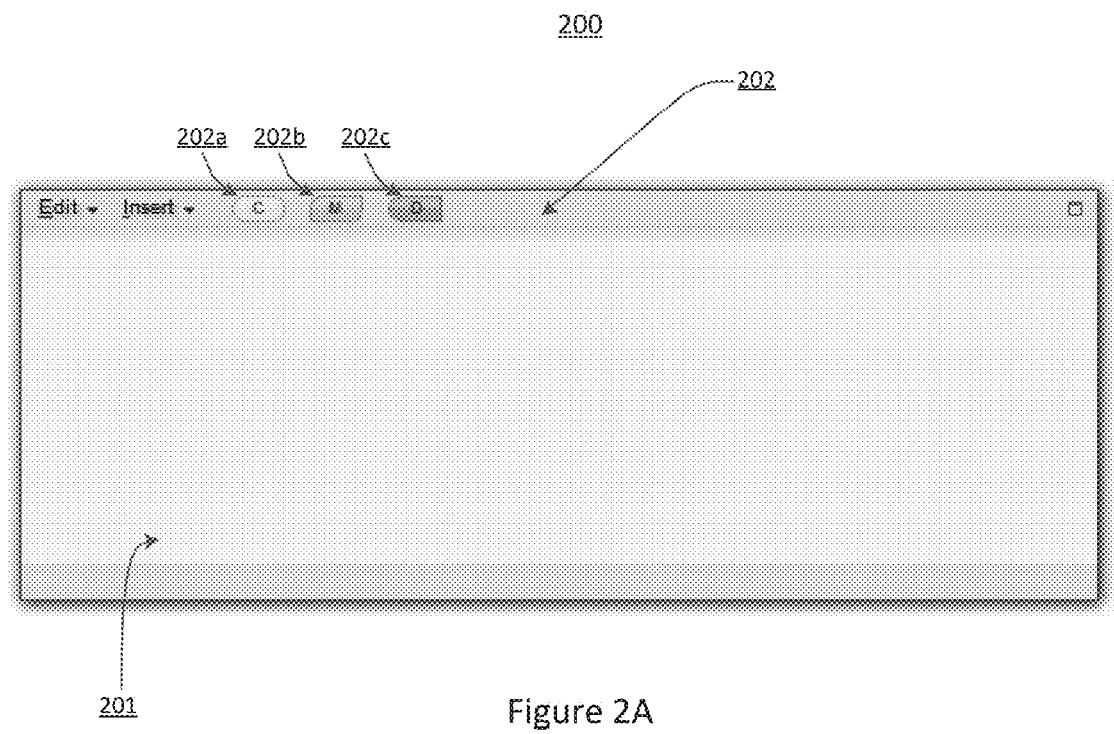
FIGS. 2A-2B illustrate an exemplary visual channel editor.

FIG. 2A illustrates an exemplary layout of a visual channel editor 200, as utilized in some embodiments. As shown, visual channel editor 200 may include a channel map 201, and an editor menu 202. Channel map 201 may include the area of visual channel editor 200 where a user graphically defines a channel. Editor menu 202 may include a number of node icons 202a-202c (representing a condition node, a mapping node, and a destination node) that a user can select (e.g., via drag and drop) to create a node within channel map 201.

Figure 2B:
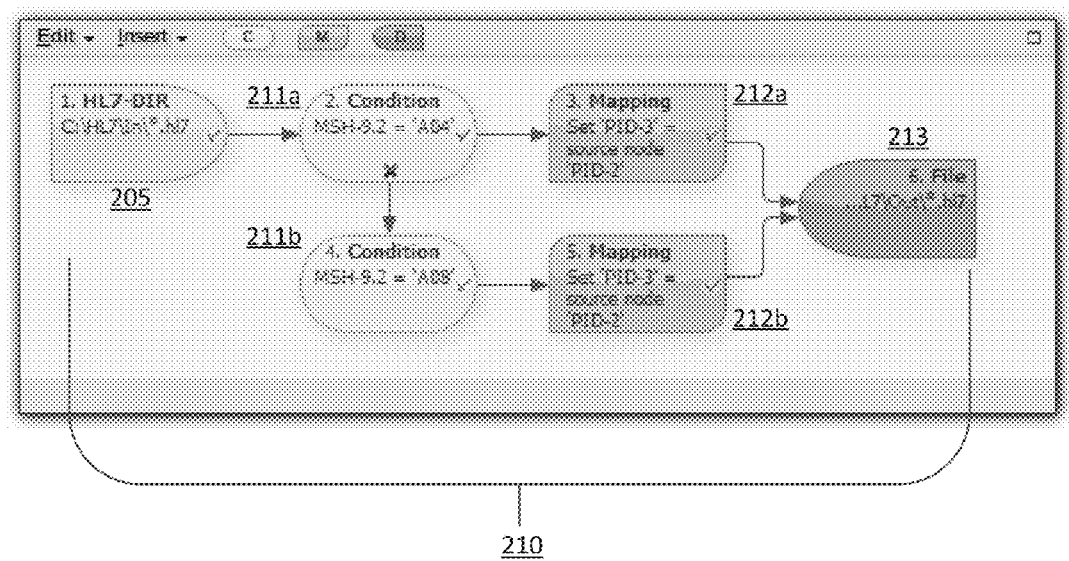

Channel map 201, as shown in FIGS. 2A, and 2B, can initially display a source node 205 by default because each channel has a single source node. A user may populate channel map 201 by selecting the node icon 202a-202c of the desired node type. In response, visual channel editor 200 may display a node in channel map 201 that can be placed anywhere within channel map 201. Once a node is added to channel map 201, links can be created between the added node and other nodes on channel map 201.

A channel can have various numbers of condition, mapping, and destination nodes. In a most basic example, a channel can comprise a source node and a destination node. In a more complex example, a channel can have multiple layers of condition nodes which filter data towards appropriate mapping and/or destination nodes. Mapping and condition nodes can be used in any order within a channel.

FIG. 2B illustrates an exemplary channel 210 within channel map 201. Channel 210 may include source node 205, condition nodes 211a-211b, mapping nodes 212a-212b, and destination node 213.

A source node 205 may specify the source of messages for the channel. Each source node may include an output connection point for defining the flow of messages from the source node. The output connection point may be in the form of a checkmark in FIG. 2B. The output connection point of a source node can be connected to multiple other nodes. In this way, a message from the source will be copied and sent to each node connected to the source node.

A condition node 211(a-b) may specify a condition (e.g. if-then) to apply to the data of incoming messages. A condition node may provide an input connection point for defining the flow of messages into the condition node, and two output connection points, a success connection point and a failure connection point, for specifying the flow of messages out from the condition node. The success connection point may be used to define the flow of messages having data that meets the condition, whereas the failure connection point is used to define the flow of messages having data that fails the condition. As shown, the success and failure connection points are in the form of a checkmark and an x respectively.

A mapping node 212(a-b) may specify a mapping to apply to the data of the messages. A mapping may include one or more operations (or mapping functions) that are applied to manipulate the data. Each mapping node may include an input and an output connection point used to create connections between the mapping node and other nodes in the channel. The output connection point may be in the form of a checkmark.

A destination node 213 may specify a destination of messages within a channel. Each destination node may include an input connection point used to create connections between the destination node and other nodes in the channel.

To create a connection between two nodes, the output connection point of one node may be selected and associated (e.g. via drag and drop) with another node. As shown in FIG. 2B, this may result in an arrow being drawn between the selected output connection point and the other node. Accordingly, in exemplary channel 210, messages are show as flowing from source node 205 into condition node 211a. Messages having data that meets the condition specified in condition node 211a may then flow to mapping node 212a, and then to destination node 213. On the other hand, messages having data that fails the condition specified in condition node 211a may flow to condition node 211b. Then, messages having data that meets the condition specified in condition node 211b may then flow to mapping node 212b and then to destination node 213, whereas messages having data that fails the condition specified in condition node 211b may not be further processed within channel 210. Connections between nodes can be configured in a many-to-many relationship. In other words, output connection points can be configured to send a message to multiple input connection points and input connection points can receive messages from multiple output connection points.

In some embodiments, to facilitate the quick identification of the characteristics of each node, a summary of the characteristics of each node can be displayed within the graphical representation of the node within channel map 201. For example, in FIG. 2B, condition node 211a includes the text "MSH-9.2='A04'" to quickly convey to the user the condition applied by the node. Similarly, for a source or destination node, an identification of the type of source or destination, and possibly a path to the source or destination, can be shown. For example, source node 205 includes the label HL7-DIR to identify that the type of source is an HL7 directory. Source node 205 also includes the path C:\HL7\In\*.h17 which indicates the path to the source directory, and the criteria for selecting files in the source directory.

Node Configuration Panel

Figure 2C:
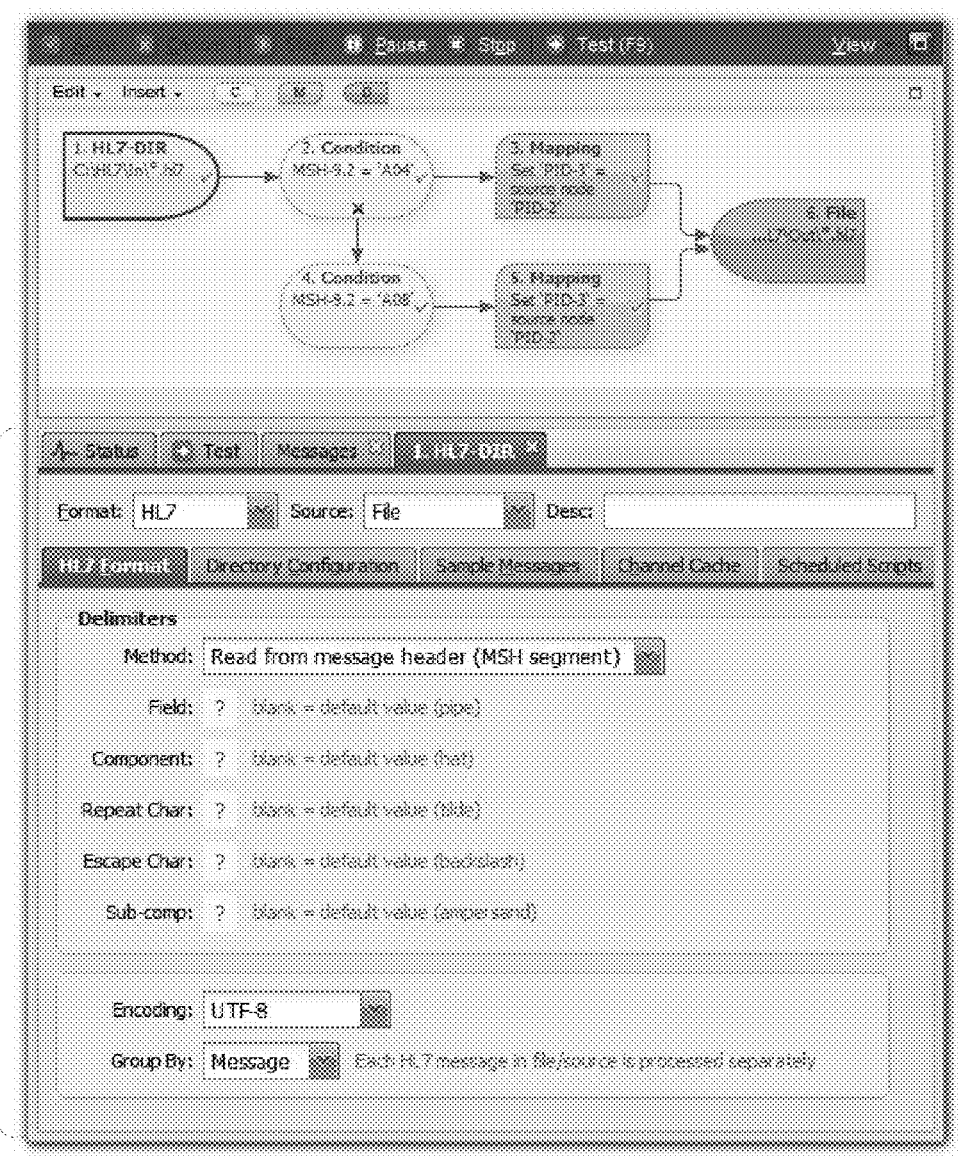
FIG. 2C illustrates an exemplary node configuration panel.

FIG. 2C illustrates visual channel editor 200 with the addition of a node configuration panel 230. Node configuration panel 230 can be displayed (or if already displayed, can be updated) when a user selects a particular node in visual channel editor 200. Node configuration panel 230 may include an area of the user interface in which various user interface controls can be displayed for selecting or specifying the configurable parameters for a given node. For example, node configuration panel 230 can provide controls such as dropdown menus, textboxes, checkboxes, etc. for receiving user input to specify configurable parameters for a given node.

Node configuration panel 230 may allow a user to define the desired functionality of a node in a graphical manner by interacting with the displayed controls. The mapping system may automatically generate scripts based on the user input to these controls. Accordingly, the user is able to create scripts graphically using simple user interface controls rather than having to write scripts in a scripting editor.

The mapping system of the present invention can provide various predefined types for each type of node. Node configuration panel 230 can display a control (e.g., a dropdown menu) which lists each of the predefined types for a selected node. For example, depending on the type of node that is selected in visual channel editor 200, node configuration panel 230 can initially display a field (or fields when a source node is selected) for selecting a particular predefined type for the selected node. Then, in response to user selection of a particular type, node configuration panel 230 displays additional controls for receiving the particular configuration settings for the selected particular type.

As described below, node configuration panel 230 can display the additional controls within a tab embedded in node configuration panel 230, or within a pop-up dialogue. Of course, other user interface containers could also be used to display these additional controls. In this manner, node configuration panel 230 may provide a greatly simplified approach for configuring nodes of a channel. Prior approaches not only required knowledge of scripting, but also required the user to understand each message format in detail to enable the user to write scripts to convert the data from one format to another. In contrast, by providing predefined types and by allowing the graphical selection/specification of parameters for these types, the described embodiments herein may greatly facilitate the creation of channels without requiring the user to have a knowledge of scripting, or an in-depth knowledge of the message formats, or other program-specific details.

Once a channel is defined, the user can save and execute the channel. When a channel is executed, messages can be read from the source location defined in the source node, processed through the channel, and written to the destination location defined in the destination node. A channel can be executed on demand or according to a schedule. For example, a channel can be configured to run at a specified time of day, or continuously (e.g., by checking the source for new messages every x seconds).

Source Node Configuration

Figure 3A:
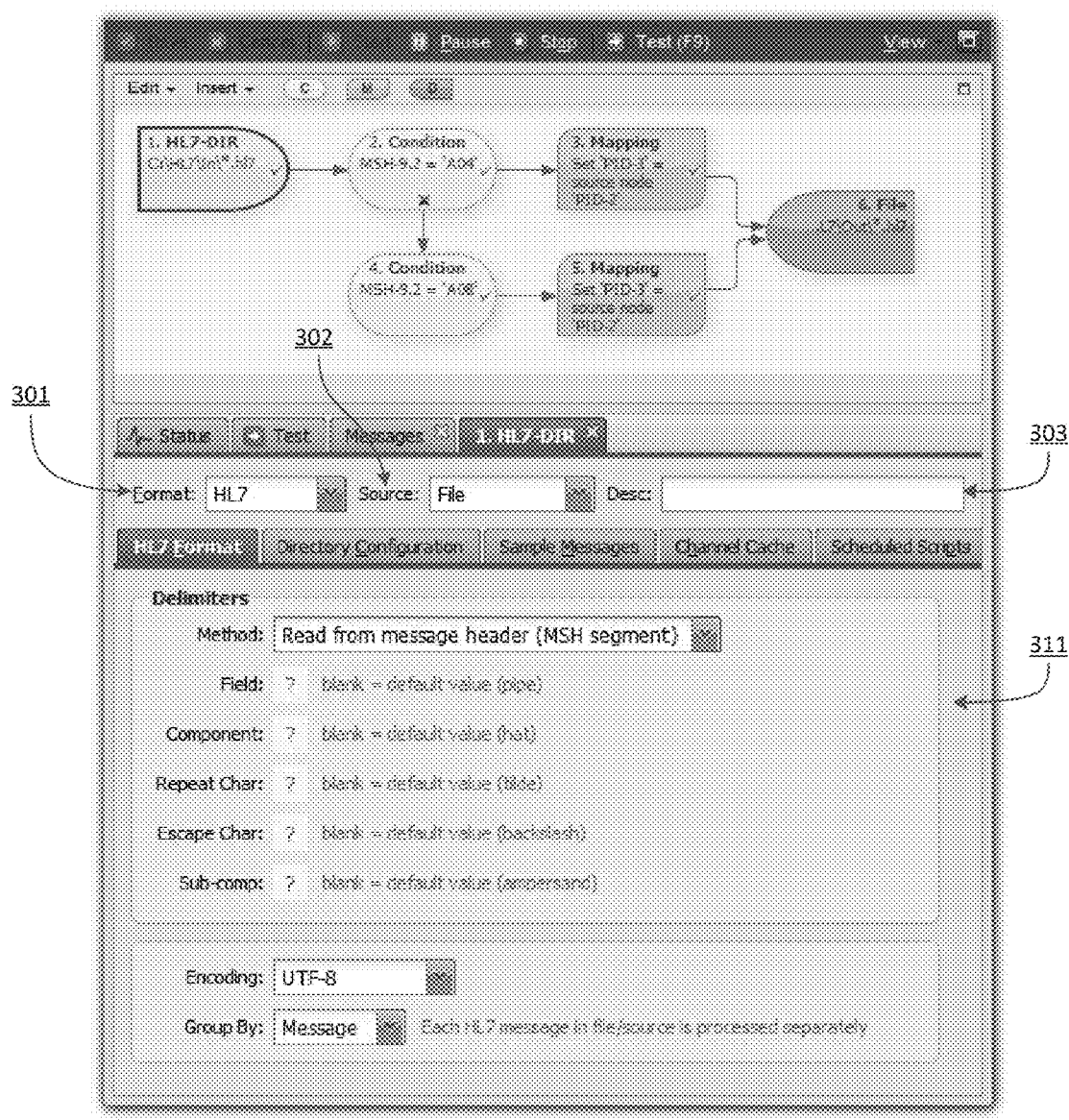
FIG. 3A illustrates the node configuration panel when a source node is selected in the visual channel editor.
Figure 3B:
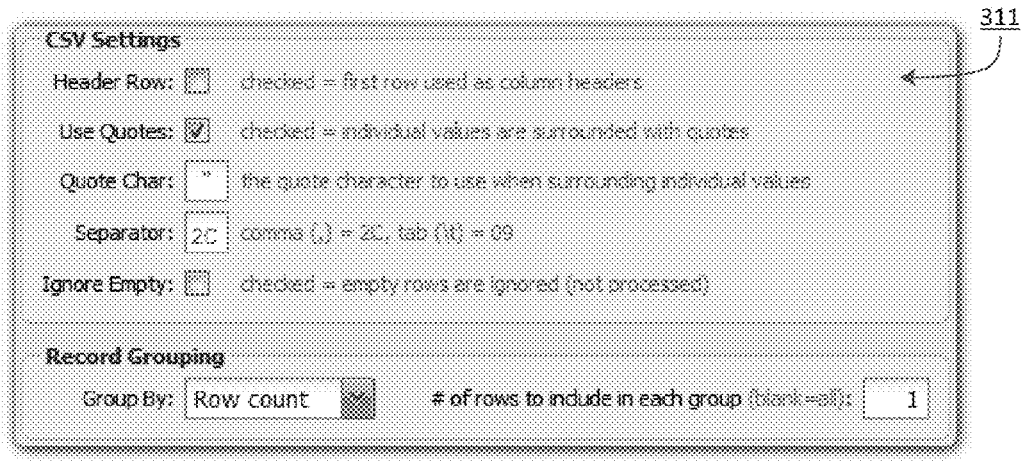
FIGS. 3B-3F illustrate an exemplary format editor.
Figure 3C:
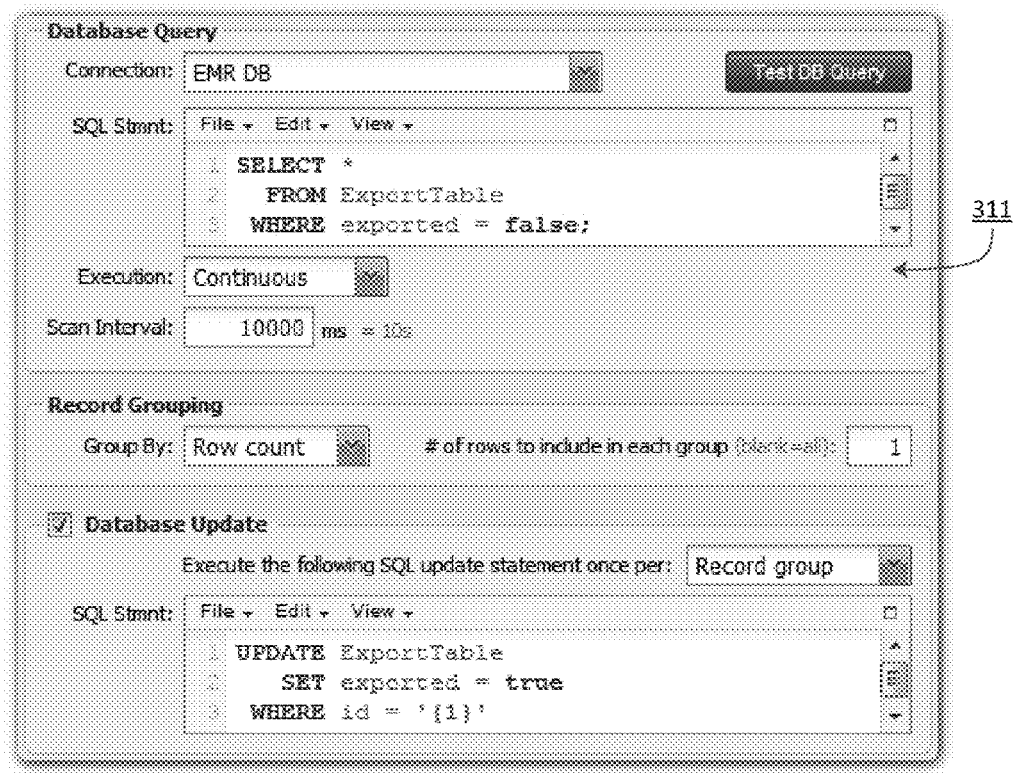
Figure 3D:
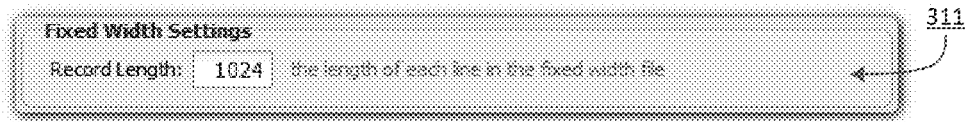
Figure 3E:
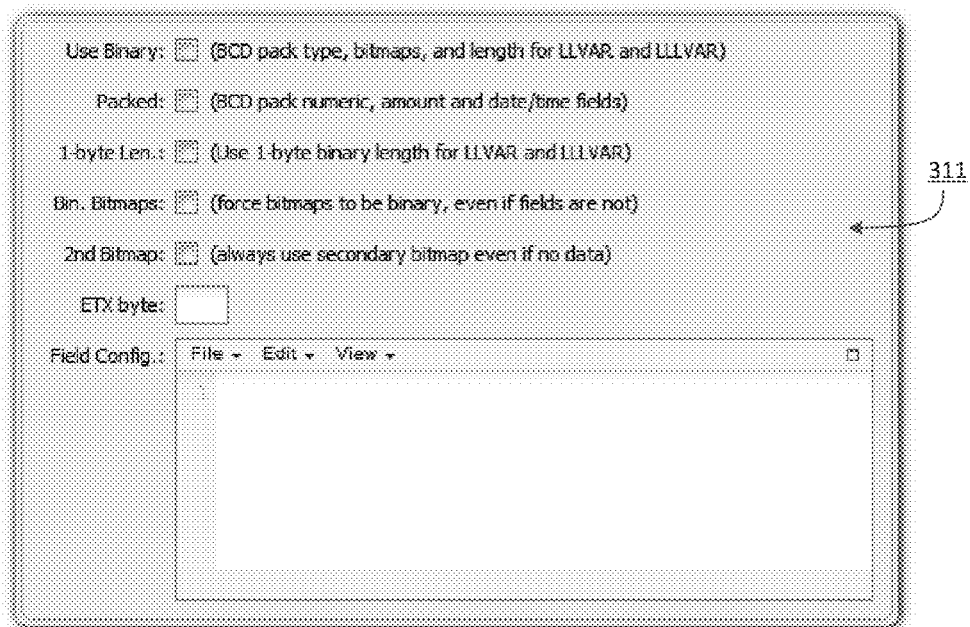
Figure 3F:
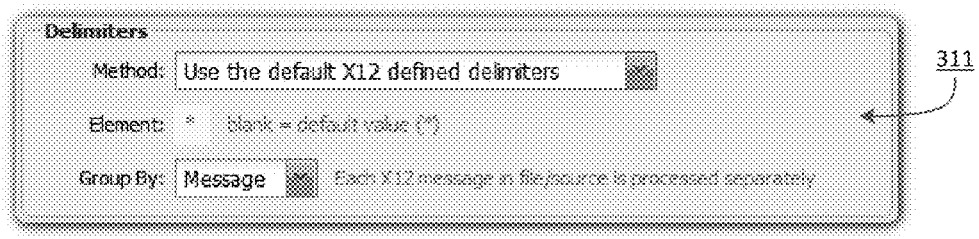
Figure 4A:
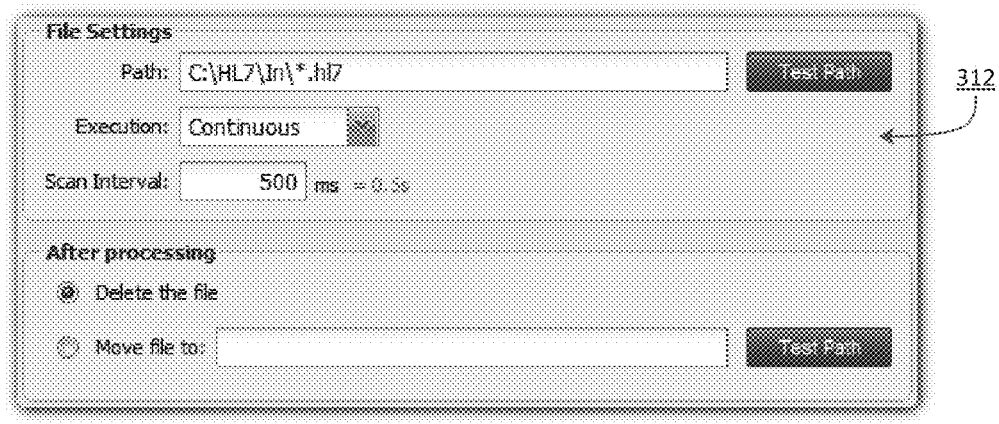
FIGS. 4A-4F illustrate an exemplary source editor.
Figure 4B:
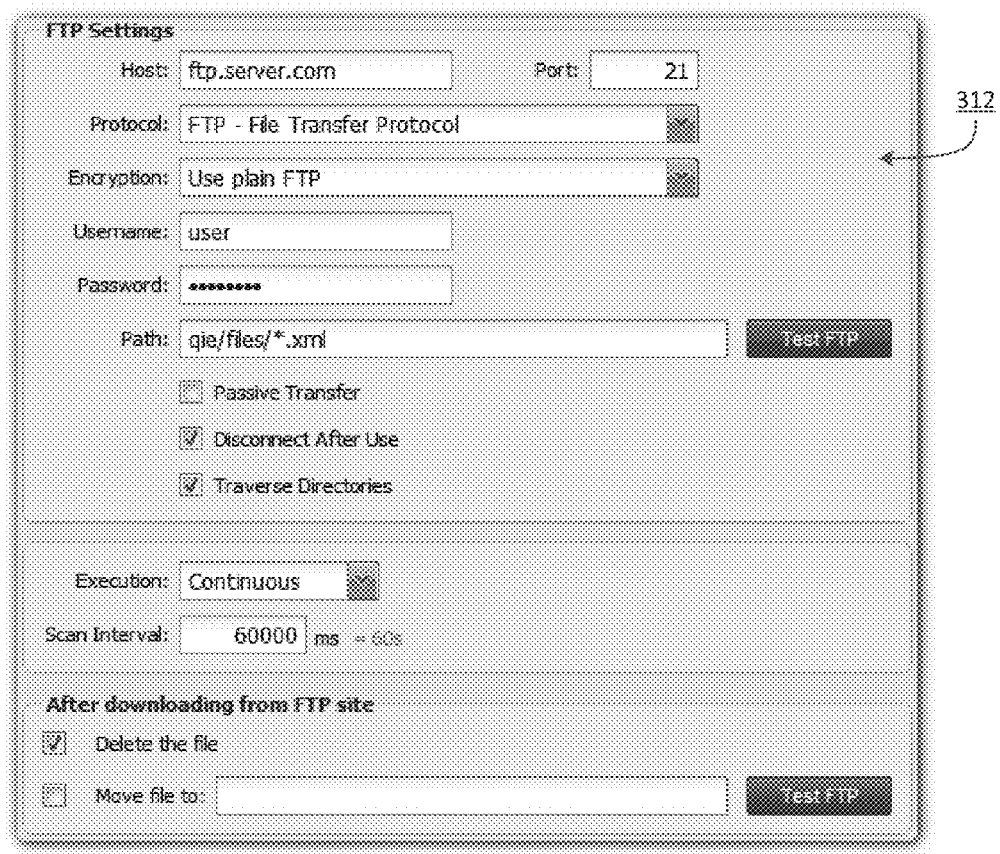
Figure 4C:
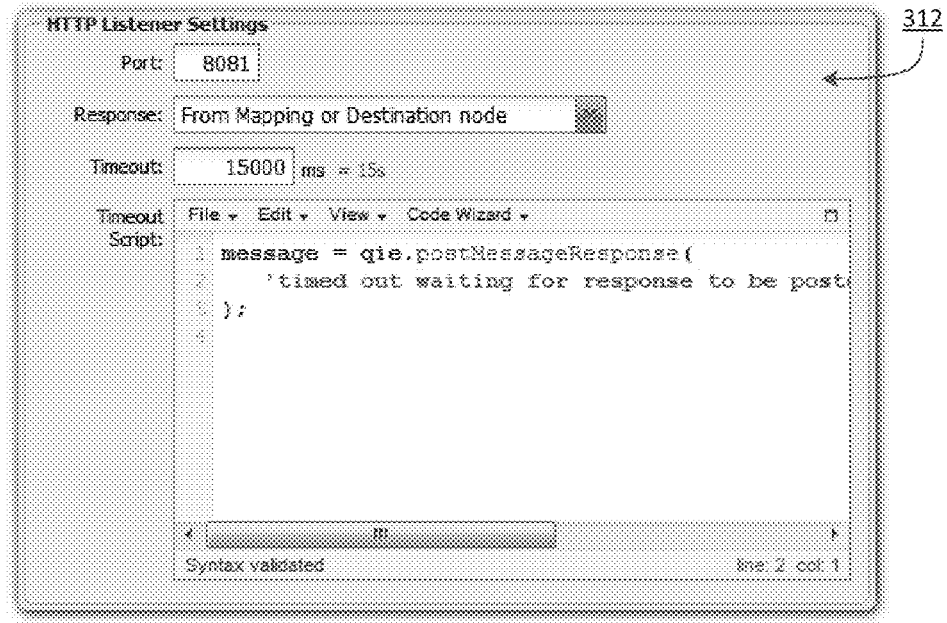
Figure 4D:
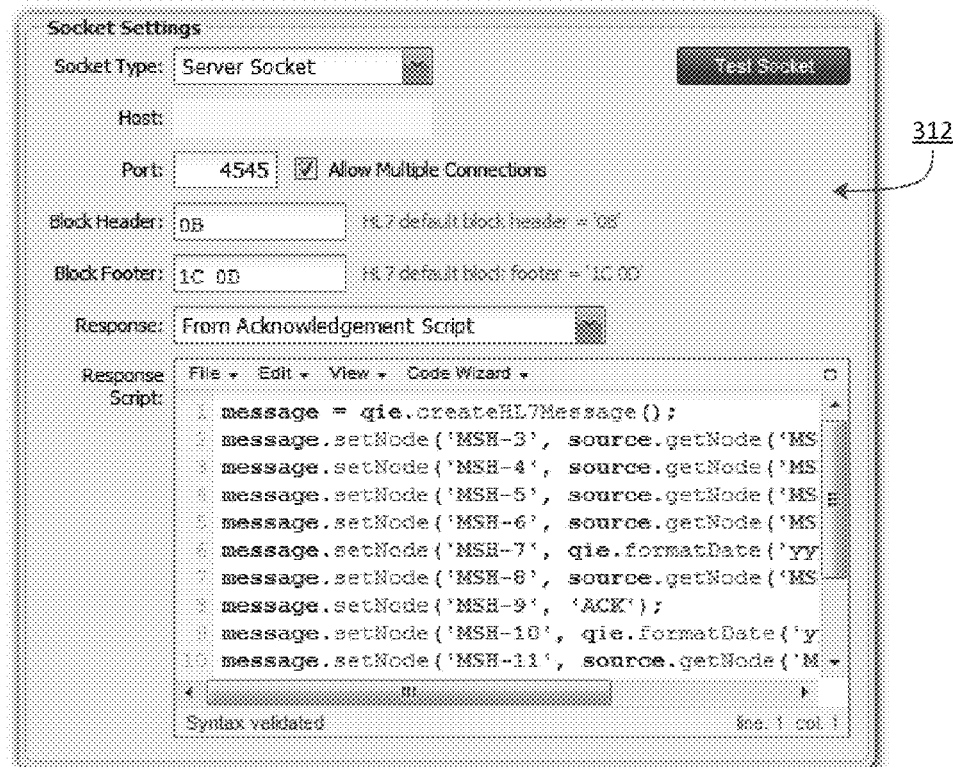
Figure 4E:
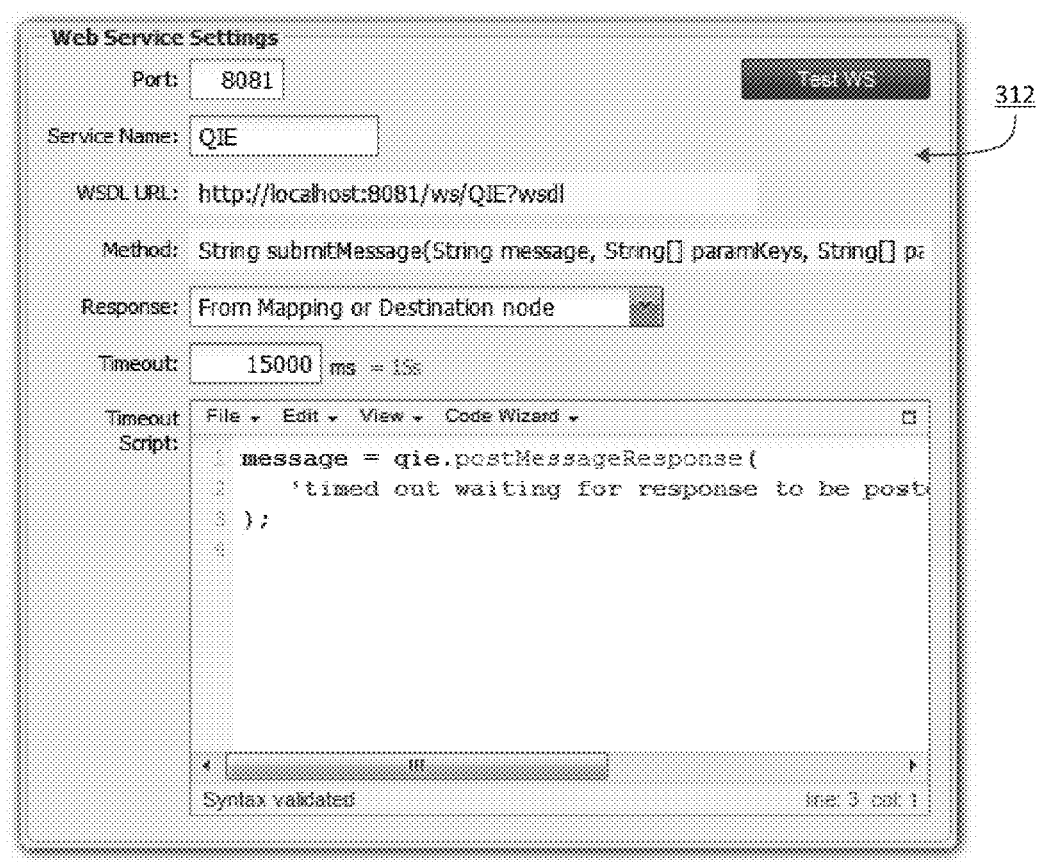
Figure 4F:
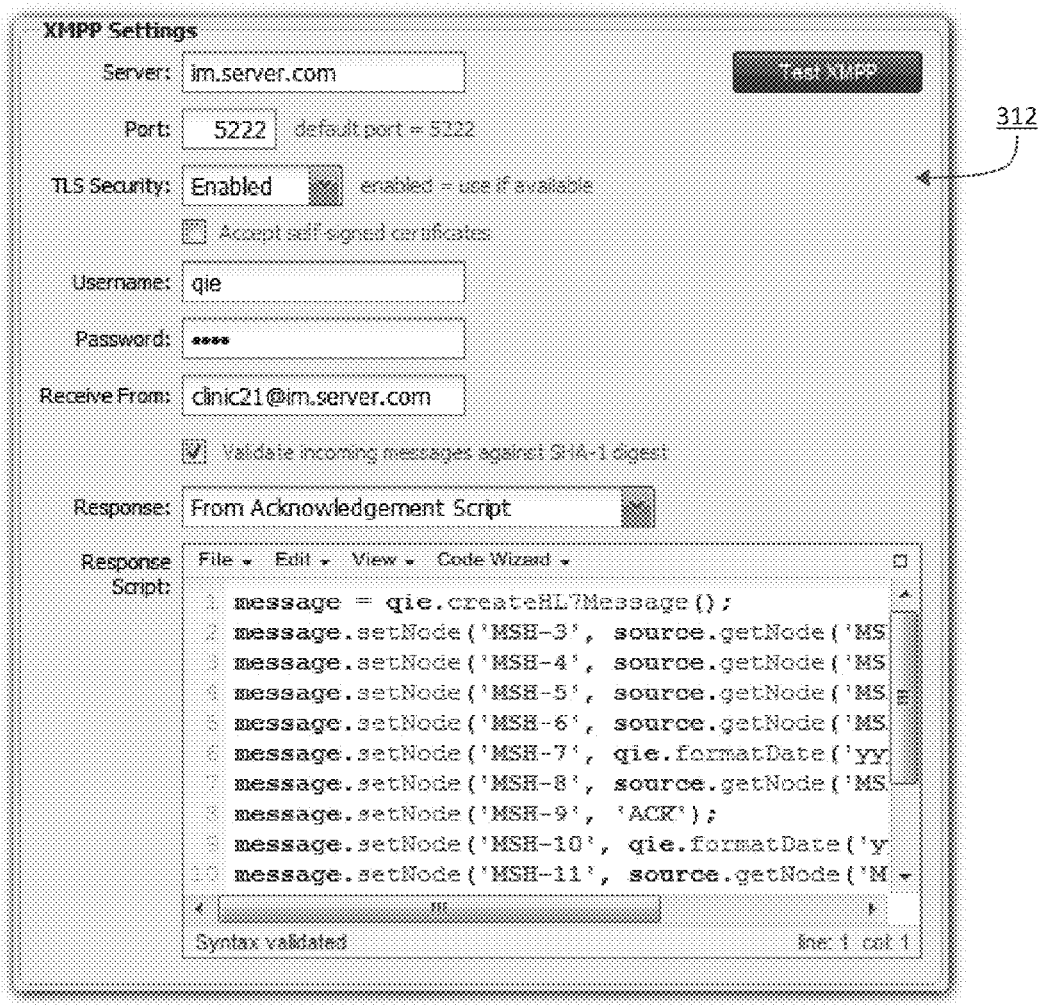

A source node may be used to define the source and format of messages to be processed by a channel. Each channel may have a single source node. As shown in FIG. 3A, when the source node 205 (FIG. 2B) is selected in visual channel editor 200 (FIG. 2B), node configuration panel 230 (FIG. 2C) may display a format field 301 and a source field 302 to allow the user to select a format and a source for messages that are to be processed by the channel. A description field 303 can also be provided to allow the user to define a custom description for the source node.

Format field 301 and source field 302 can each provide a list of predefined format and source types respectively. For example, in some embodiments, format field 301 can provide the following predefined formats commonly used by HIT systems: CSV, database query results, fixed width, HL7, ISO 8583, JSON, plain text, XML, and X12 (ASC X12). Similarly, in some embodiments, source field 302 can provide the following predefined sources: a file source, an FTP source, an HTTP source, a socket source, a web service source, and an XMPP source.

The format field 301 and the source field 302 may each have a corresponding editor, format editor 311 and source editor 312, respectively, for receiving user input to specify the configurable parameters for the selected format or source. When a particular format or source is selected in format field 301 or source field 302 respectively, the corresponding editor may display appropriate controls for receiving the user input. Format editor 311 and source editor 312 can be displayed as embedded tabs within node configuration panel 230 (FIG. 2C) (e.g., as format editor 311 shown in FIG. 3A), or as dialogues (e.g., as format editor 311 shown in FIGS. 3B-3F and source editor 312 shown in FIGS. 4A-4F). Of course, other user interface containers could also be used. The other editors described below can also be displayed in like manners.

FIGS. 3A-3F illustrate examples of format editor 311 when the user has selected HL7, CSV, database query results, fixed width, ISO 8583, and X12 respectively in format field 301. Similarly, FIG. 4A-4F illustrate examples of source editor 312 when the user has selected file, FTP, HTTP, socket, web service, and XMPP respectively in source field 302 (FIG. 3A). The appendix includes a description of the various format and source types and the associated controls displayed in the corresponding editor for a particular implementation of the present invention.

Mapping Node Configuration

Figure 5A:
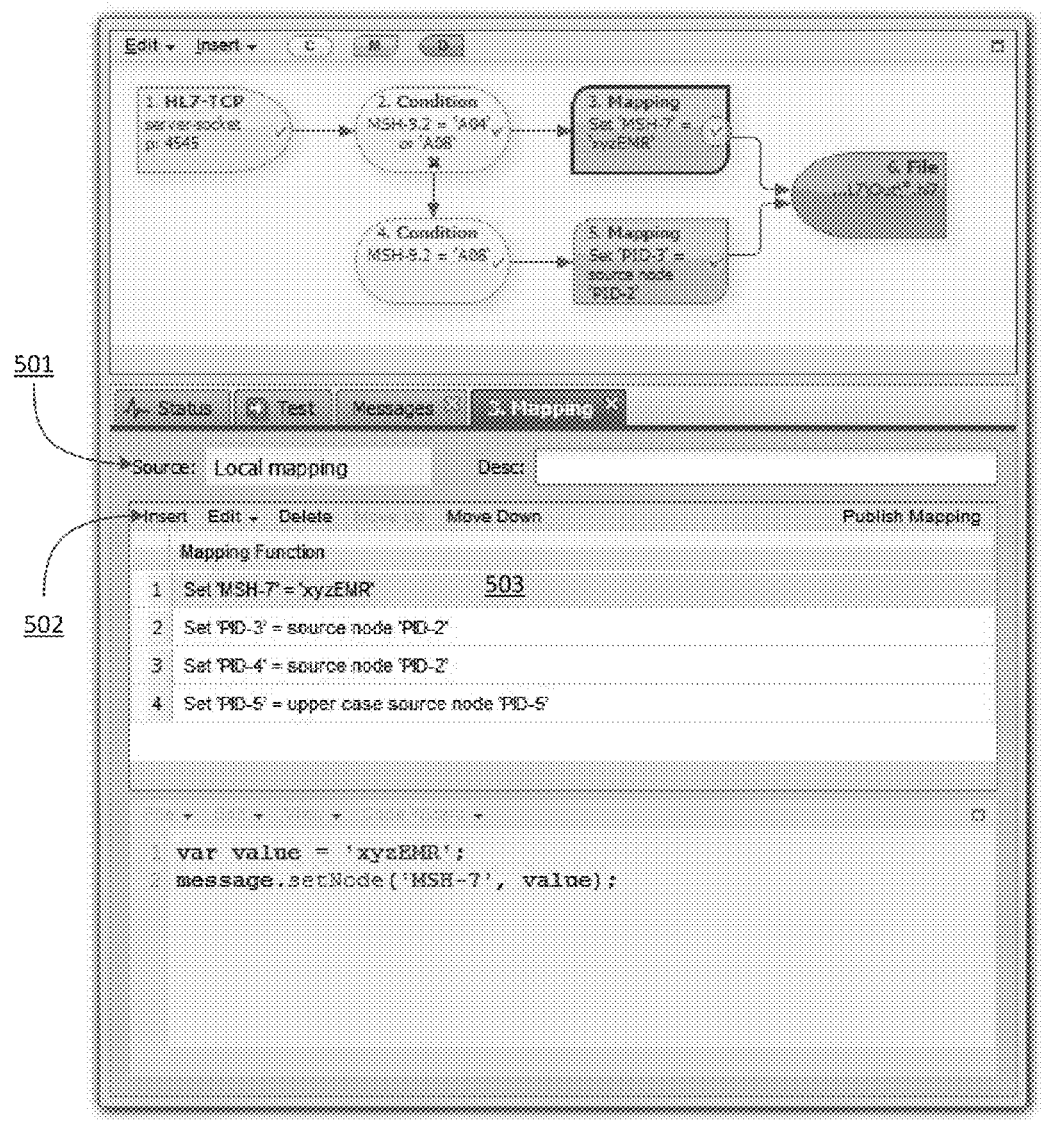
FIG. 5A illustrates the node configuration panel when a mapping node is selected in the visual channel editor.

Mapping nodes may define the mapping functions to apply to data of messages flowing through the mapping node. As shown in FIG. 5A, when a mapping node is selected in visual channel editor 200 (FIGS. 2A-2C), node configuration panel 230 (FIG. 2C) may display a source field 501 for defining the source for the mapping node. Node configuration panel 230 can also display a defined mapping function field 503 which lists any mapping functions that have been defined for the mapping node. In some embodiments, the source for a mapping node can be a local mapping, a published mapping, or a copy of a published mapping. A local mapping may be a mapping that is local to the channel being displayed within visual channel editor 200. A published mapping may be a mapping that has been published for use in any applicable channel. A copy of a published mapping may be a published mapping that is copied and made available as a local mapping (e.g., to allow the published mapping to be editing and customized for the particular channel).

With each of the different types of mapping node sources, a mapping may include an ordered list of mapping functions. Mapping functions may define logic for performing a data manipulation on the data of messages passing through the mapping node. Once a mapping node source is specified in source field 501, the user can select the insert button 502 to add a mapping function to the mapping node. In FIG. 5A, four mapping functions are shown in defined mapping function field 503 as already having been inserted. Once a mapping function is added, it can be edited or deleted using the buttons shown.

Figure 5B:
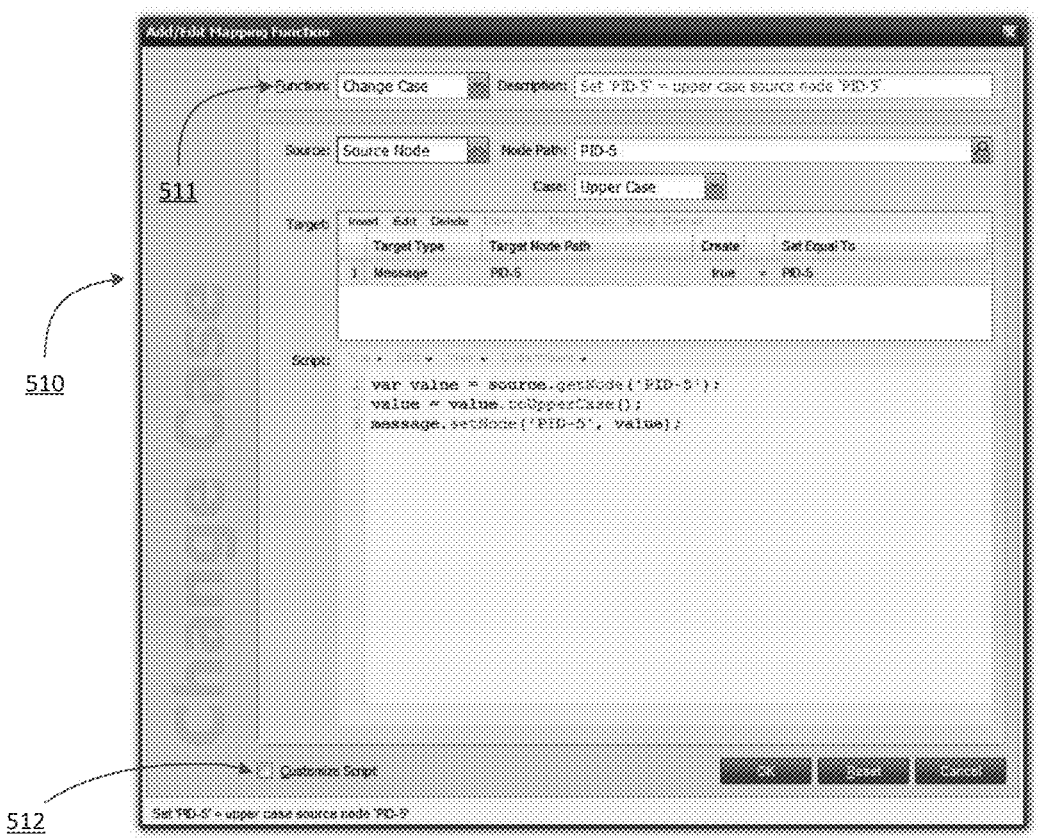
FIGS. 5B-5C illustrate an exemplary mapping editor.
Figure 5C:
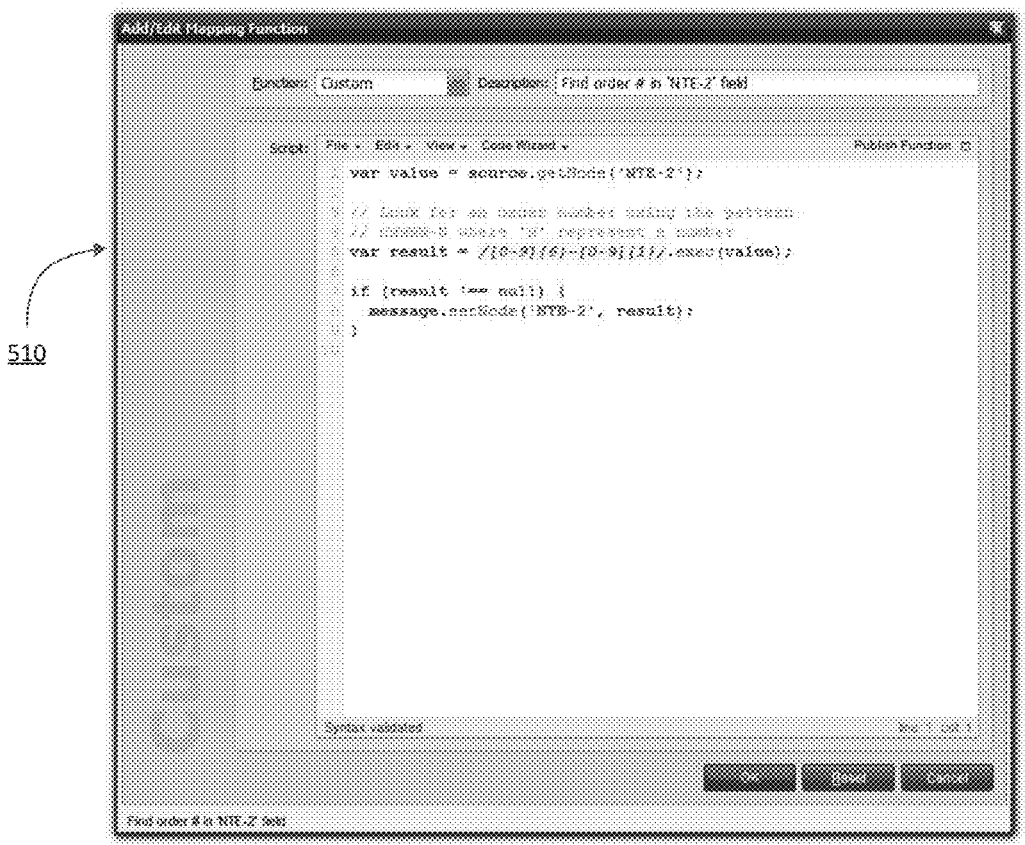

When insert button 502 is selected, mapping editor 510 may be displayed. FIGS. 5B-5C display two exemplary views of a mapping editor 510. Mapping editor 510 may include a function field 511 in which a user can select a type of mapping function. The remaining fields displayed within mapping editor may be dependent on the type of mapping function selected within function field 511.

To facilitate defining mapping functions, the mapping system can provide various built-in mapping functions that a user can select to perform many of the most common data manipulations. These built-in mapping functions can include the following functions: change case, custom, date/time, database query, new message, published, replace, standard, substring, table lookup, template, and web service. Details regarding each of these functions, including the configurable parameters displayed within mapping editor 510 for each mapping function, are provided in the appendix.

As examples, FIGS. 5B-5C illustrate mapping editor 510 when the change case mapping function and the custom mapping function respectively have been selected in function field 511. As shown in FIG. 5B, when the change case mapping function is selected in function field 511, source, node path, case, and target fields may be displayed in mapping editor 510. Accordingly, the described embodiments may facilitate the definition of mapping functions by allowing the user to select/specify appropriate values for each of the fields of a predefined mapping function, and in response, a script (or scripts) for performing the desired mapping function may be automatically generated. In the example in FIG. 5B, the automatically generated script for performing a change case mapping function is shown in the script field.

In this manner, the user may be relieved of having to write scripts to define mapping functions. However, mapping editor 510 may still provide the flexibility to customize an automatically generated script or write custom scripts using a scripting editor. By clicking customize script checkbox 512, the script field may become a scripting editor in which the user can directly modify the automatically generated script. Similarly, as shown in FIG. 5C, when custom is selected in function field 511, mapping editor may display a scripting editor in which the user can write custom scripts. Accordingly, node configuration panel 230 (FIG. 2C) may provide a simplified graphical interface to allow the user to define mapping functions for a mapping node by interacting with common user interface controls, while at the same time maintaining the robustness provided by a scripting environment to allow low level script definition as desired.

Condition Node Configuration

Figure 6A:
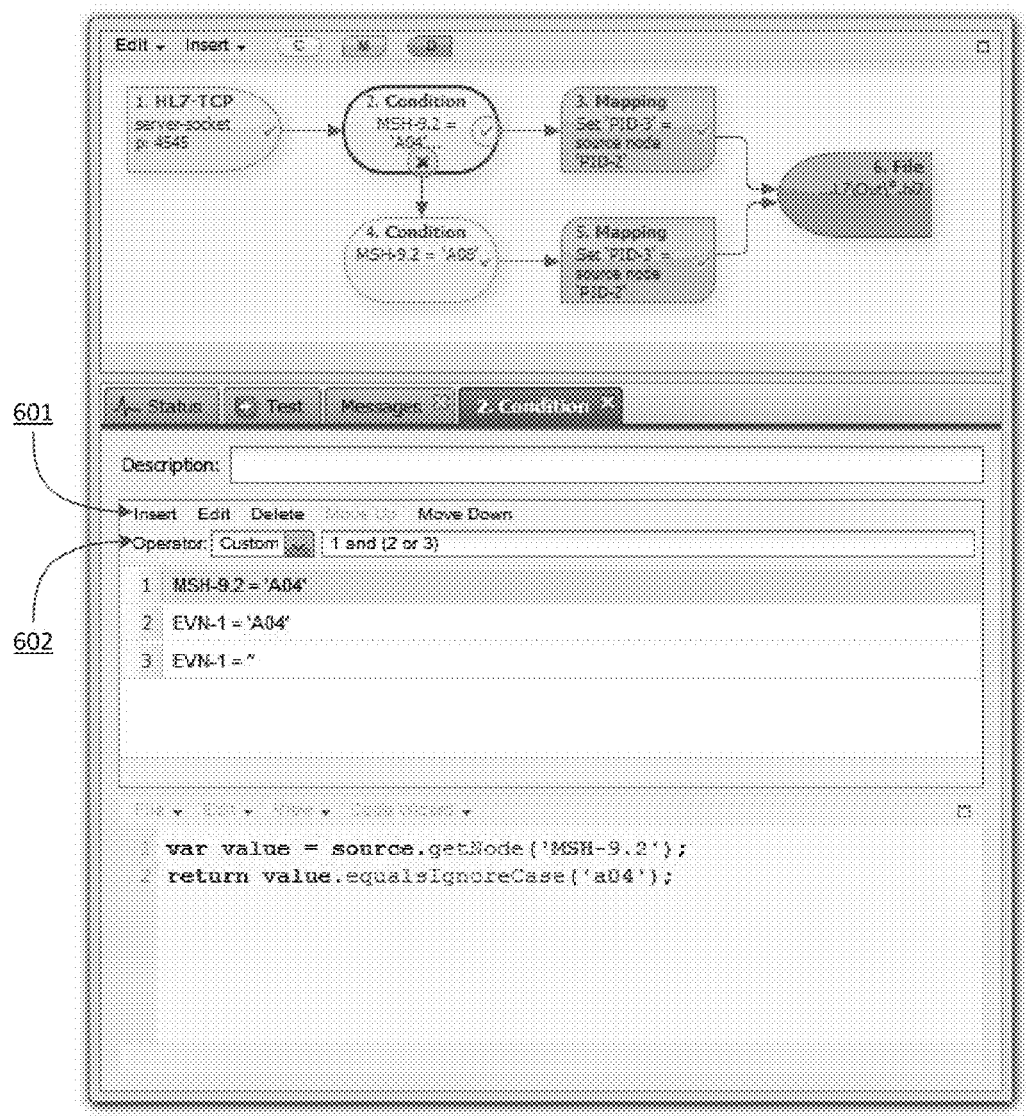
FIG. 6A illustrates the node configuration panel when a condition node is selected in the visual channel editor.

Condition nodes may be used to control the flow of messages through a channel. Condition nodes may specify one or more conditions applied to the data of messages to determine whether the messages should flow through the success connection point or the failure connection point of the condition node. As shown in FIG. 6A, when a condition node is selected within visual channel editor 200 (FIGS. 2A-2C) node configuration panel 230 (FIG. 2C) displays an insert button 601 and an operator field 602. Insert button 601 is used, similar to insert button 501, to create conditions in the condition node. When insert button 601 is selected, a condition editor 610 is displayed as is shown in FIGS. 6B-6D.

Operator field 602 may be used to define the logic for applying conditions when more than one condition has been defined in a condition node. For example, operator field 602 can provide predefined Boolean operators for performing AND and OR logic on the specified conditions. Operator field 602 can also provide a custom option to allow the user to specify custom logic for applying the conditions. For example, in FIG. 6A, three conditions may be defined for the node, and the user has defined custom logic of "1 and (2 or 3)" indicating that a message having data that matches condition 1 and either condition 2 or condition 3 will pass to the success connection point.

Figure 6B:
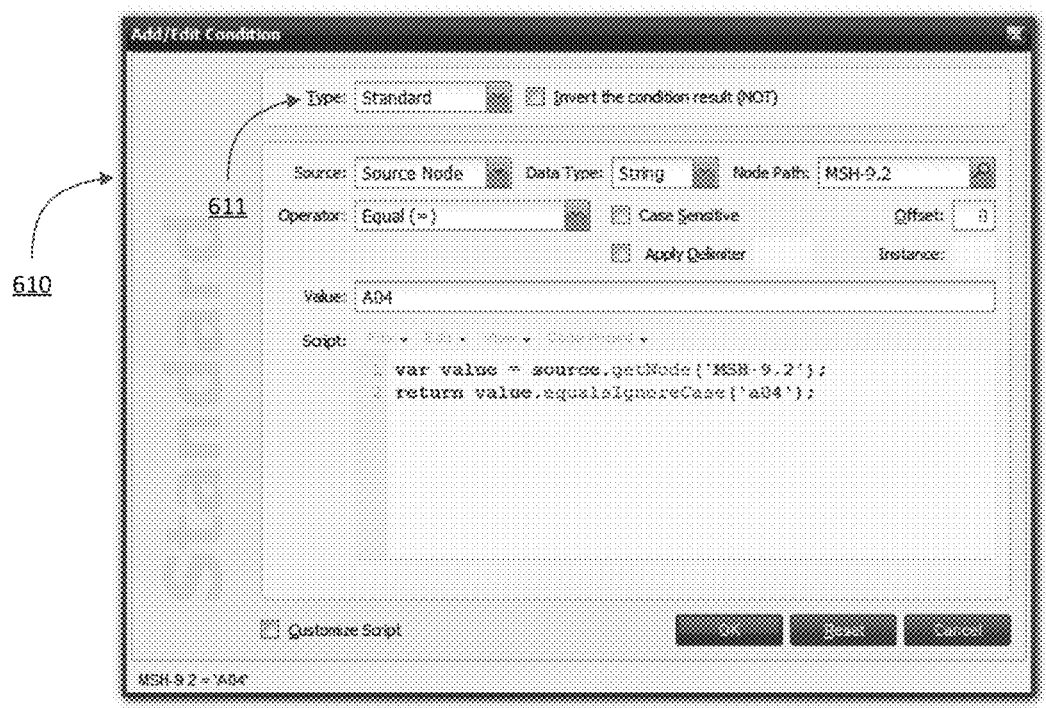
FIGS. 6B-6D illustrate an exemplary condition editor.
Figure 6C:
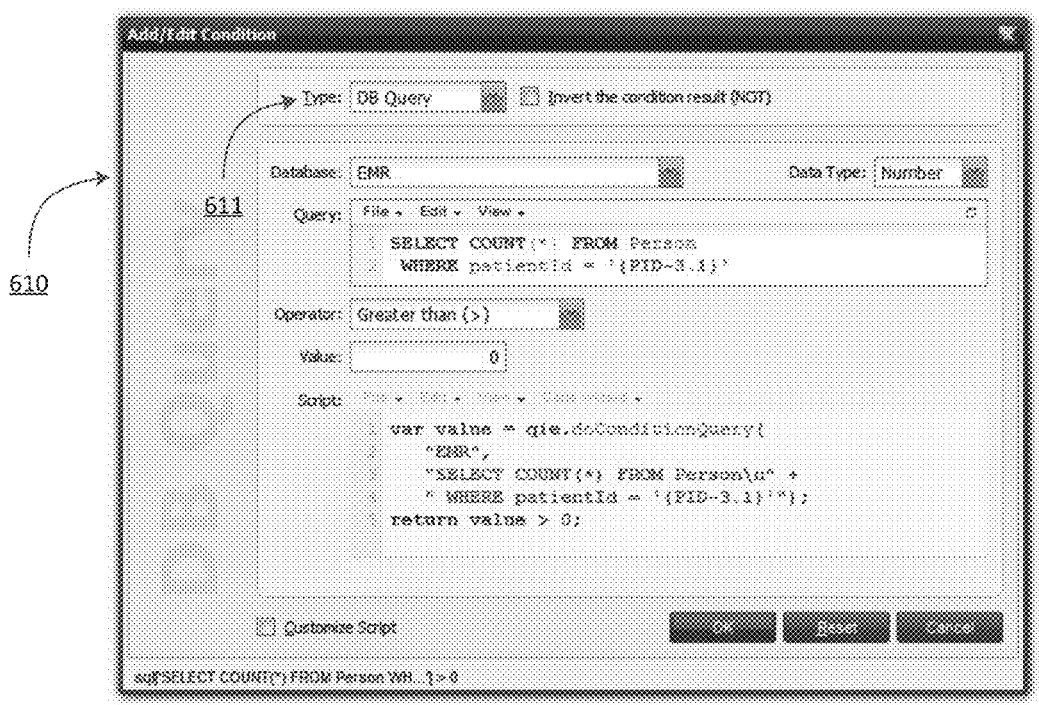
Figure 6D:
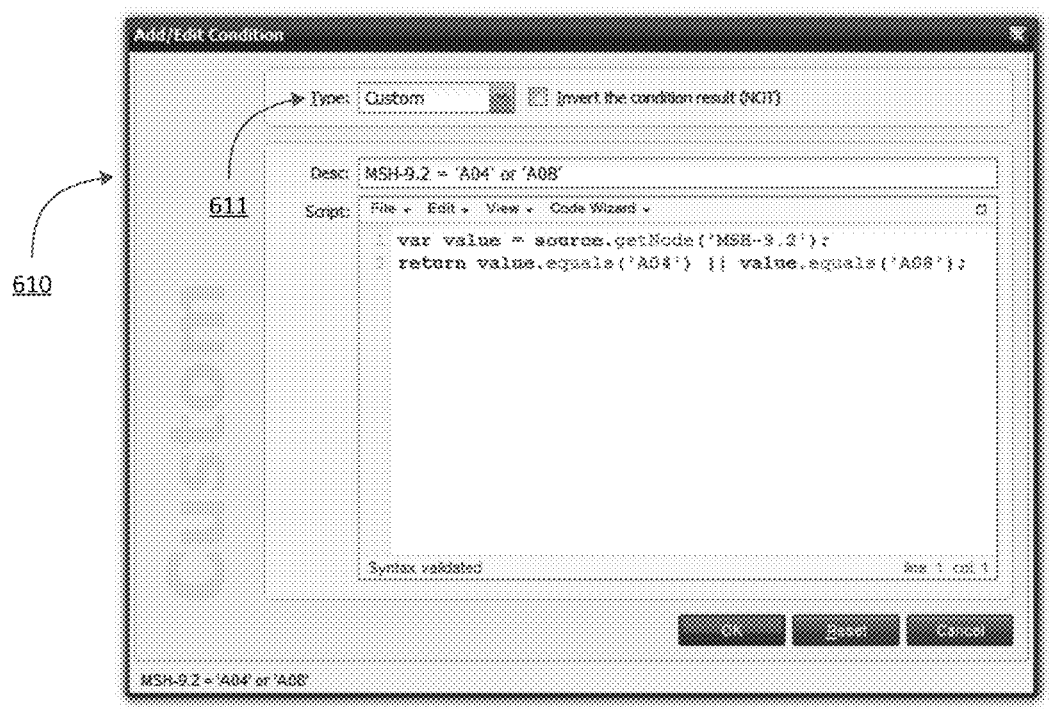

FIGS. 6B-6D illustrate exemplary views of condition editor 610. Condition editor 610 may include a type field 611 as identified in FIG. 6B. Type field 611 may list various predefined conditions that a user can select. In some embodiments, these predefined conditions can include standard, db query, and custom conditions. Condition editor 610 may display various fields for specifying configurable parameters depending on the type of condition selected in type field 611. Details regarding each of the fields and corresponding configurable parameters are provided in the appendix.

Destination Node Configuration

Figure 7A:
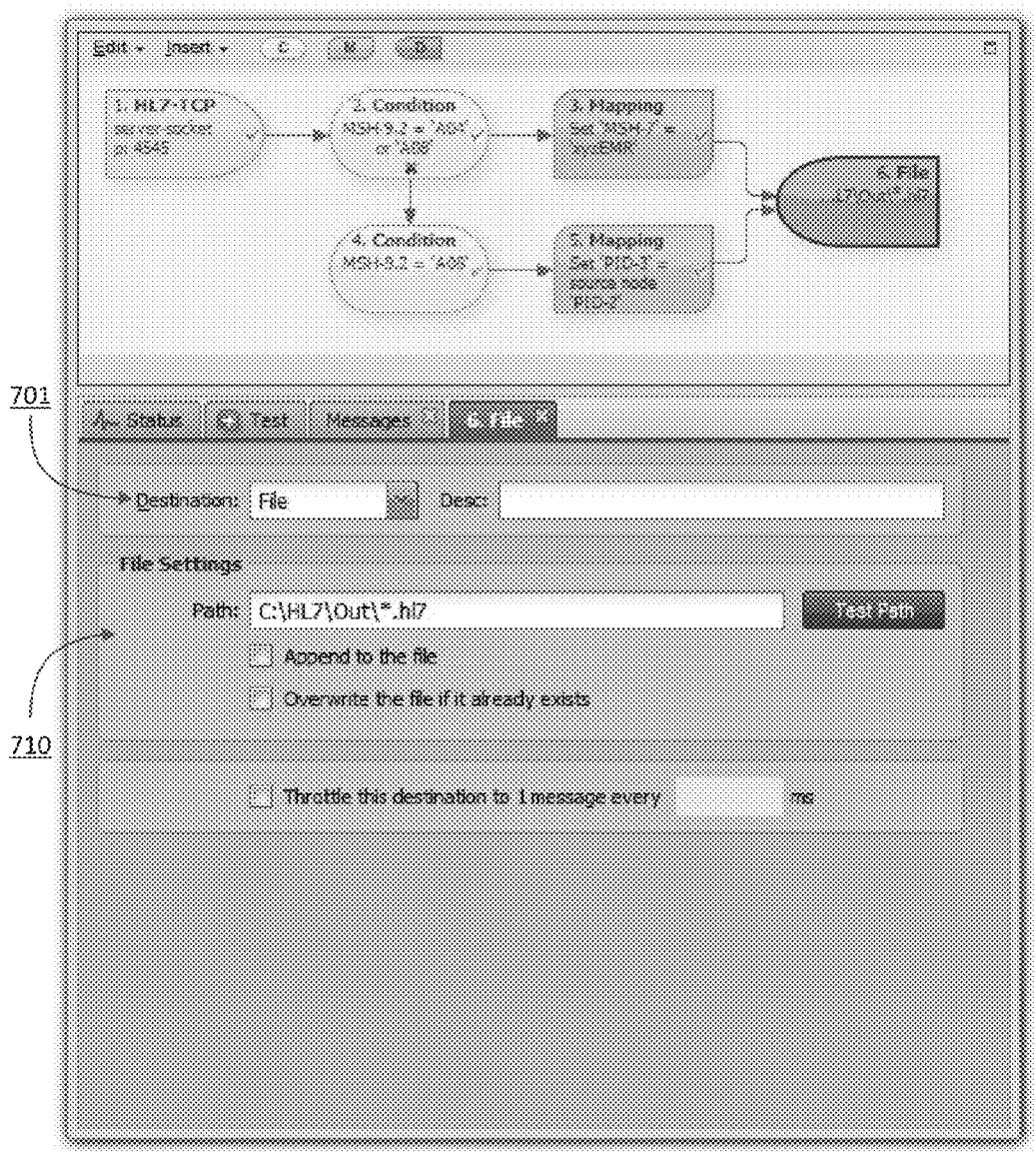
FIG. 7A illustrates the node configuration panel when a destination node has been selected in visual channel editor.

Destination nodes may be used to define where messages are sent after being processed through a channel. Each channel may include one or more destination nodes. As shown in FIG. 7A, when a destination node is selected in visual channel editor 200 (FIGS. 2A-2C), node configuration panel 230 (FIG. 2C) may display a destination field 701 to allow the user to select a destination for messages that have been processed in the channel. In some embodiments of the invention, the following destinations can be provided: a database destination, a discard destination, a file destination, an FTP destination, a socket destination, a web service destination, and an XMPP destination.

Figure 7B:
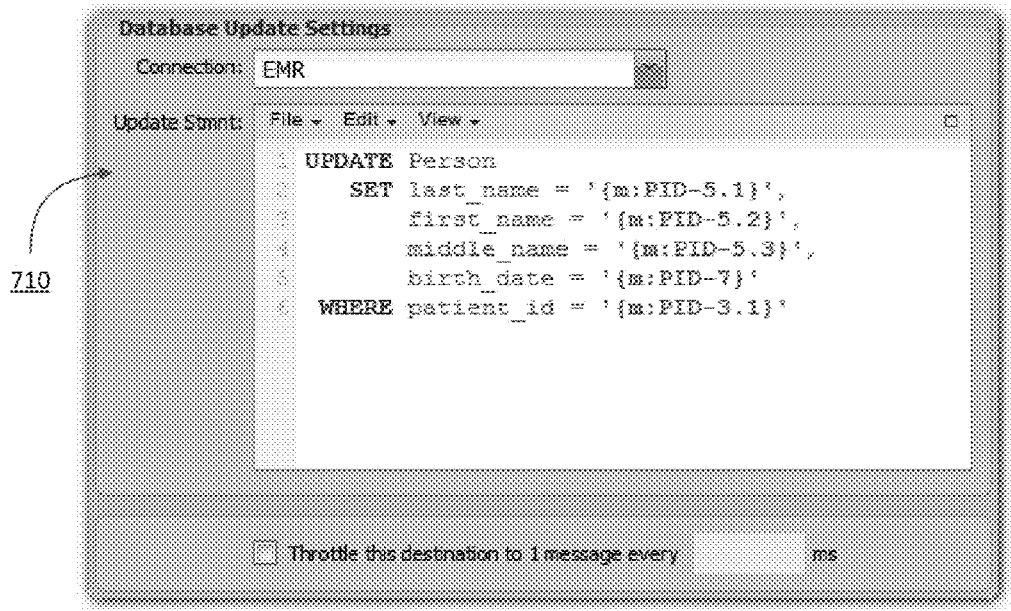
FIGS. 7B-7D illustrate an exemplary destination editor.
Figure 7C:
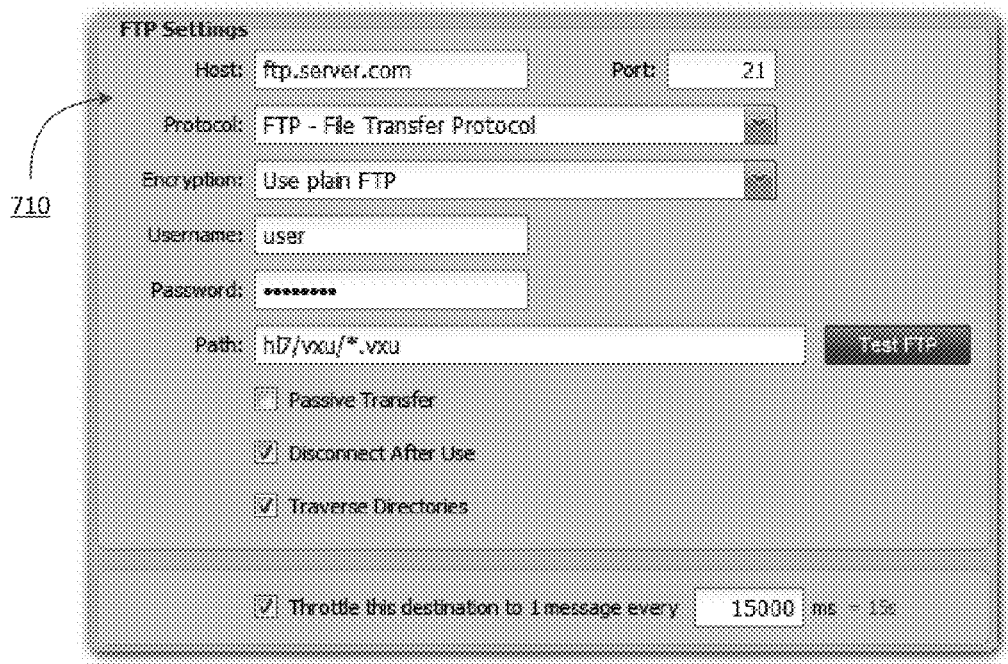
Figure 7D:
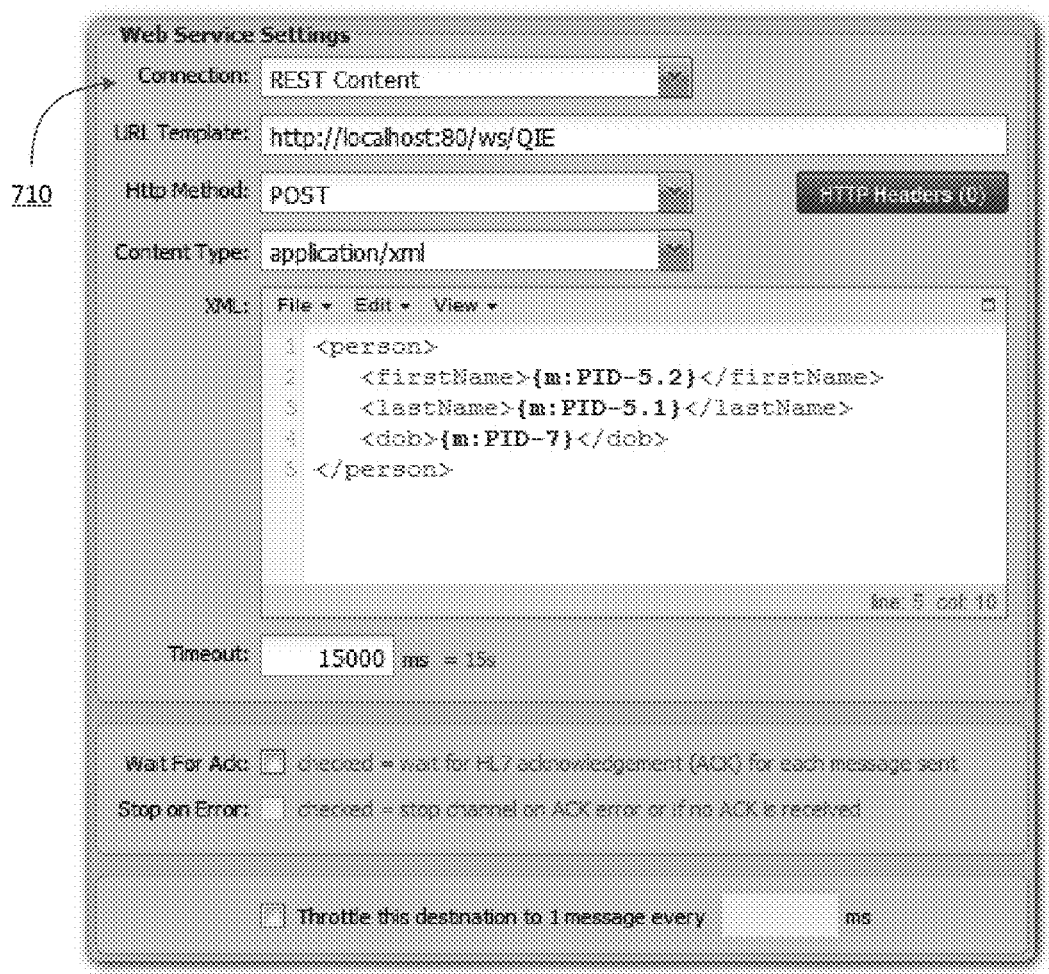

When a destination is selected in destination field 701, a destination editor 710 may be displayed. Destination editor 710 may include various controls, depending on the type of destination selected in destination field 701, for specifying the configurable parameters of the selected destination. FIG. 7A illustrates an exemplary view of destination editor 701 for a file destination when destination editor is embedded in node configuration panel 230, and FIGS. 7B-7D illustrate exemplary views of destination editor 710 as a separate dialogue for a database, FTP, and web service destination respectively. The appendix provides a detailed description of various destination types and their associated configurable parameters for a particular implementation of the present invention.

Node Path Lookup Dialogue

Figure 8A:
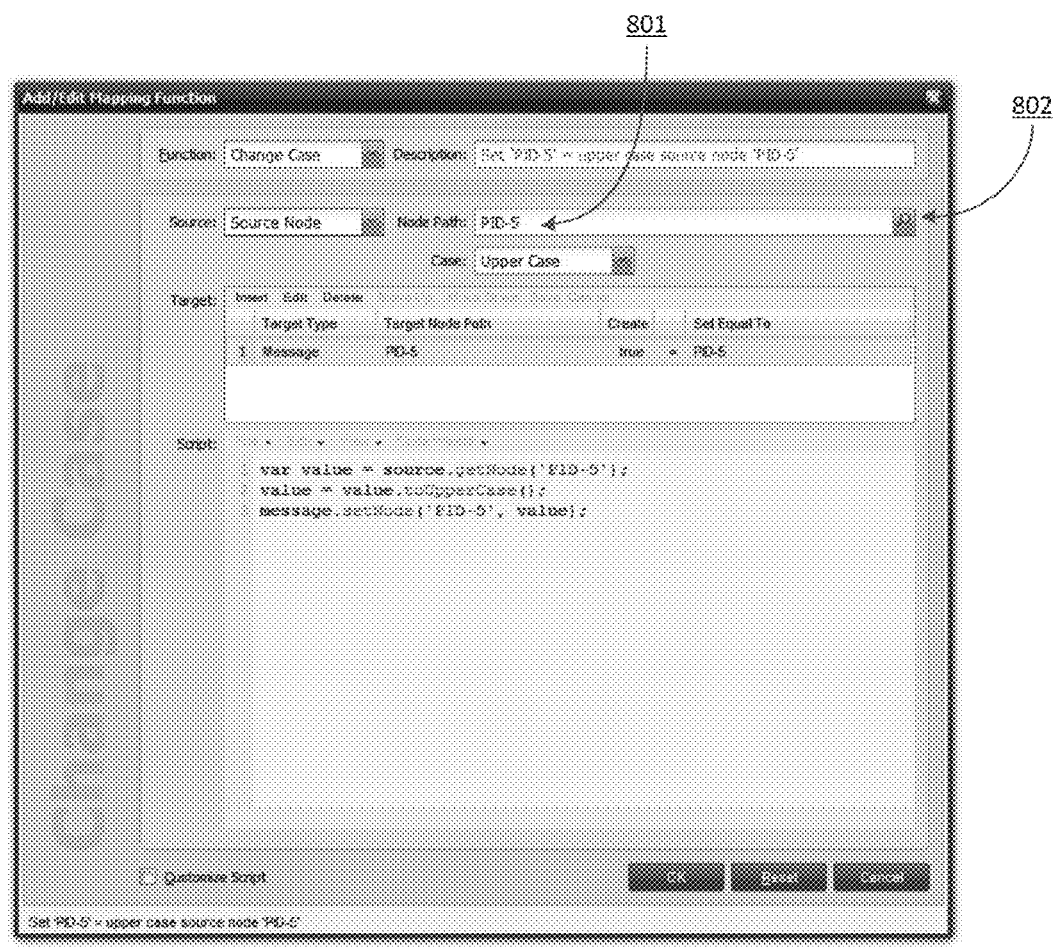
FIG. 8A illustrates an exemplary node path field in an editor.
Figure 8B:
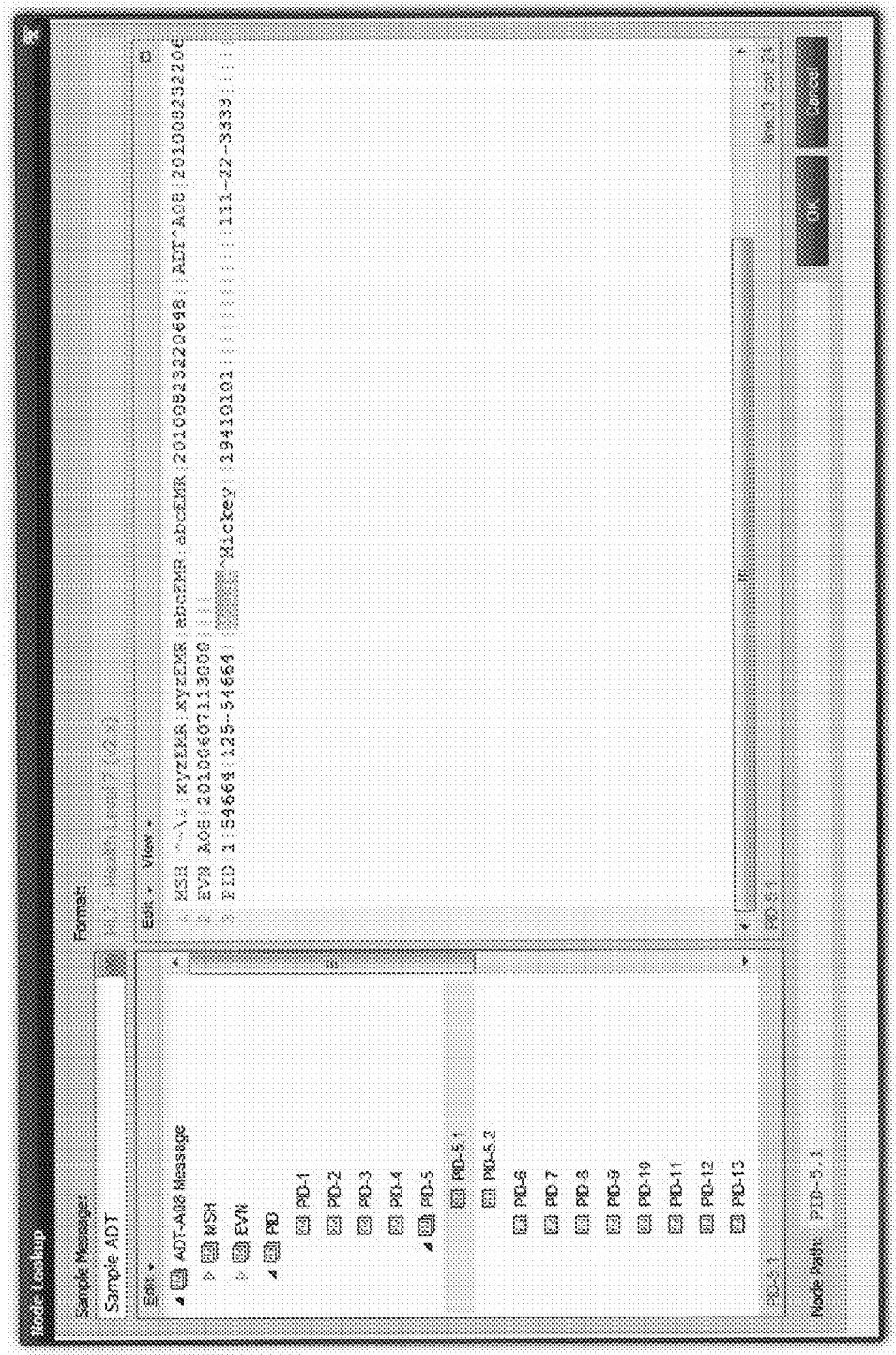
FIG. 8B illustrates an exemplary node path lookup.

With some mapping functions and conditions, it may be necessary to identify a node or element in a message to which the mapping function or condition applies. In such cases, mapping editor 510 or condition editor 610 may include a node path field. For example, FIG. 8A illustrates node path field 801 in mapping editor 510. A node path can be directly entered into node path field 801. However, many users may not know the required syntax for specifying a node or an element in a node path. Therefore, the mapping system of the present invention provides a node path lookup dialogue 810, as shown in FIG. 8B, to allow the graphical creation of node paths.

As shown in FIG. 8A, node path field 801 may include a node path lookup button 802. When node path lookup button 802 is selected, node path lookup dialogue 810 may be displayed, as shown in FIG. 8B. Node path lookup dialogue 810 may include a sample message frame 811 that displays a sample message associated with the channel, and a tree view frame 812 that displays the hierarchical structure of the sample message. Sample messages may be messages of the appropriate format for the channel. The appendix provides further detail regarding sample messages. The user can select a node or element for the node path by selecting the desired node or element in either the tree view frame or the sample message frame. Once selected, a node path to the selected node or element may be displayed within node path Field 801 (FIG. 8A). As can be seen, using node path lookup dialogue 810, the user does not need to know how to write node paths (i.e., the user does not need to understand the syntax for identifying nodes in a particular message format).

Exemplary Methods

Figure 9:
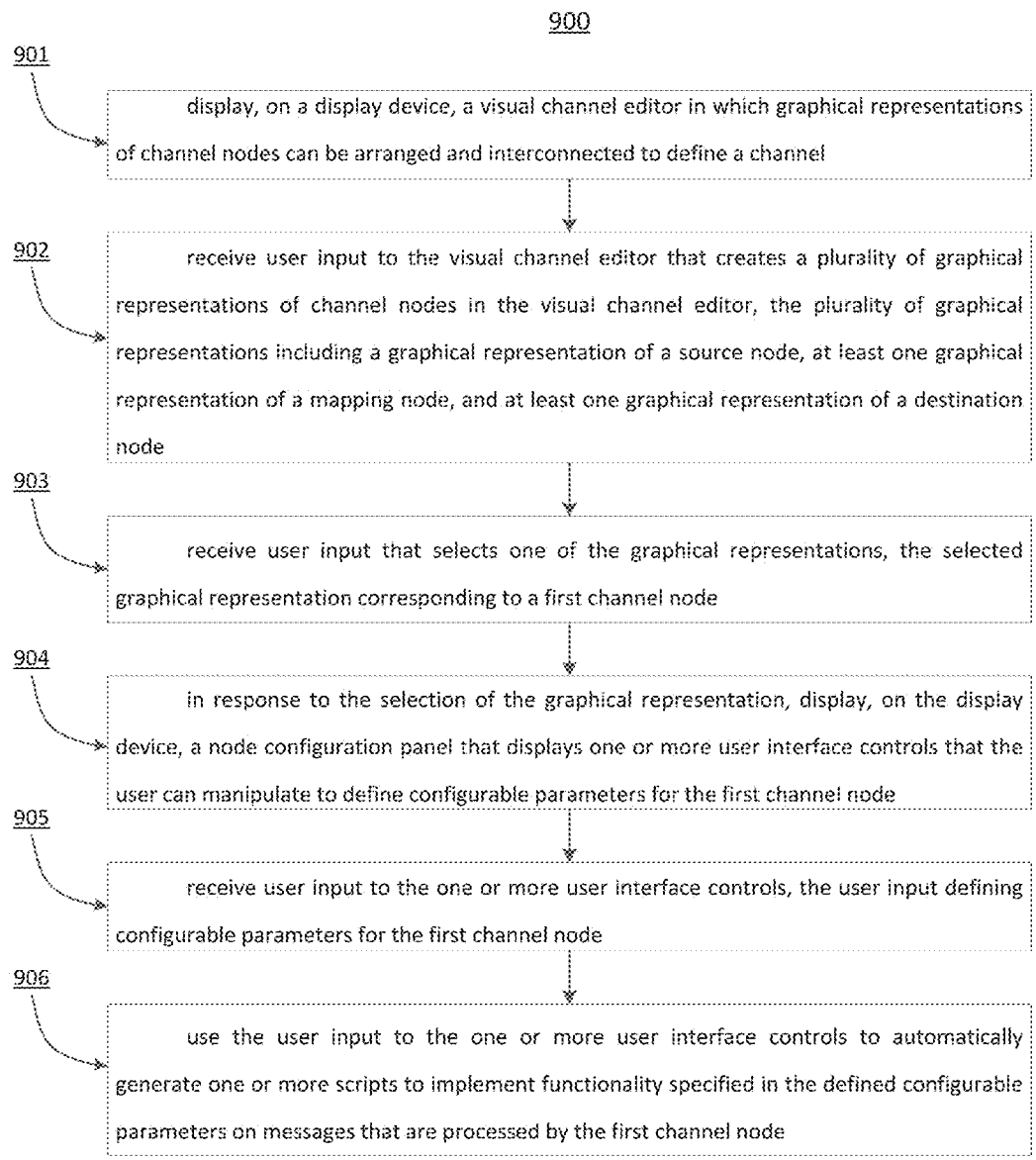
FIG. 9 illustrates a flowchart of an exemplary method for graphically defining a channel for processing messages.

FIG. 9 illustrates a flowchart of an exemplary method 900 for graphically defining a channel for processing messages. Exemplary methods, such as method 900 may include an act 901 of displaying, on a display device, a visual channel editor in which graphical representations of channel nodes can be arranged and interconnected to define a channel. For example, visual channel editor 200 (FIGS. 2A-2C) can be displayed to a user on any type of display device connected to a computer system executing the mapping system.

Method 900 may also include act 902 of receiving user input to the visual channel editor that creates a plurality of graphical representations of channel nodes in the visual channel editor. The plurality of graphical representations may include a graphical representation of a source node and at least one graphical representation of a destination node. The plurality of graphical representations may also include at least one graphical representation of a mapping or condition node. For example, a user can interact with the node icons 202a-202c (FIG. 2A) to position graphical representations of channel nodes in channel map 201 (FIG. 2A). Similarly, a user can position default graphical representations that are already displayed in channel map 201 (FIG. 2A).

Act 903 may be receiving user input that selects one of the graphical representations. The selected graphical representation corresponding to a first channel node. For example, a user can click on (or otherwise select) any graphical representation in channel map 201 (FIG. 2A) of visual channel editor 200 (FIGS. 2A-2C). Act 904 may include, in response to the selection of the graphical representation, displaying, on the display device, a node configuration panel that displays one or more user interface controls that the user can manipulate to define configurable parameters for the first channel node. For example, node configuration panel 230 (FIG. 2C) can be displayed with the user interface controls corresponding to the type of channel node selected.

Act 905 of receiving user input to the one or more user interface controls, the user input defining configurable parameters for the first channel node, may also be included. For example, a user can select a particular parameter from a field (e.g., a particular predefined type for the selected channel node from a dropdown menu). Method 900 may also include act 906 of using the user input to the one or more user interface controls to automatically generate one or more scripts to implement functionality specified in the defined configurable parameters on messages that are processed by the first channel node. For example, if the first channel node were a source node, one or more scripts could be automatically generated from user input to the user interface controls that were displayed based on the type of format and source selected in the format field 301 (FIG. 3A) and source field 302 (FIG. 3A), respectively.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed to be limiting in any manner.

What is claimed:

1. One or more non-transitory computer storage media storing computer executable instructions which when executed perform a method in a computer system for graphically defining a channel for processing messages, the method comprising:
    displaying, on a display device, a visual channel editor in which graphical representations of channel nodes can be arranged and interconnected to define a channel;
    receiving user input to the visual channel editor that creates a plurality of graphical representations of channel nodes in the visual channel editor, the plurality of graphical representations including a graphical representation of a source node and at least one graphical representation of a destination node;
    receiving user input that selects one of the graphical representations, the selected graphical representation corresponding to a first channel node;
    in response to the selection of the graphical representation, displaying, on the display device, a node configuration panel that displays one or more user interface controls that the user can manipulate to define configurable parameters for the first channel node, wherein the one or more user interface controls displayed in the node configuration panel include one or more fields that each list a number of predefined types for the first channel node that a user can select, and
    wherein the first channel node is a source node, and wherein the one or more fields include a source field and a format field, the source field for defining a source of messages to be processed in the channel, and the format field for defining a format for the messages;
    receiving user input to the one or more user interface controls, the user input defining configurable parameters for the first channel node; and
    using the user input to the one or more user interface controls to automatically generate one or more scripts to implement functionality specified in the defined configurable parameters on messages that are processed by the first channel node.

2. The one or more computer storage media of claim 1, wherein the plurality of graphical representations further include at least one graphical representation of a mapping node or a condition node.

3. The one or more computer storage media of claim 1, wherein the user input that creates the plurality of graphical representations includes user input that defines connections between the plurality of graphical representations.

4. The one or more computer storage media of claim 1, wherein the method further comprises:
    receiving user input that selects a first predefined type in one of the one or more fields; and
    in response to the selection of the first predefined type, displaying one or more additional user interface controls that the user can manipulate to define configurable parameters specific to the first predefined type.

5. The one or more computer storage media of claim 4, wherein the one or more additional user interface controls include a node path field for receiving a node path, the node path field including a button for launching a node path lookup dialogue, the method further comprising:
    receiving user input that selects the button;
    displaying the node path lookup dialogue that includes a sample message;
    receiving user input that selects a node in the sample message; and
    automatically creating a node path to the selected node in the node path field.

6. The one or more computer storage media of claim 4, wherein the one or more additional user interface controls include a node path field for receiving a node path, the node path field including a button for launching a node path lookup dialogue, the method further comprising:

receiving user input that selects the button;

displaying the node path lookup dialogue that includes a tree view comprising a hierarchical listing of the nodes of a sample message;

receiving user input that selects a node in the tree view; and automatically creating a node path to the selected node in the node path field.

7. The one or more computer storage media of claim 1, wherein the first channel node is a mapping node, and wherein the one or more fields include a source field for defining the source of a mapping for the mapping node.

8. The one or more computer storage media of claim 1, wherein the plurality of graphical representations further includes at least one condition node, and the first channel node is a condition node, and wherein the one or more fields include an operator field for defining logical operations to perform on multiple conditions that are defined for the condition node.

9. The one or more computer storage media of claim 1, wherein the first channel node is a destination node, and wherein the one or more fields include a destination field for defining the destination for messages that are processed through the channel.

10. The one or more computer storage media of claim 1, wherein the first channel node is a source node, and the predefined types include one or more of CSV, database query results, fixed width, HL7, ISO 8583, JSON, plain text, XML, or X12 (ASC X12).

11. The one or more computer storage media of claim 1, wherein the first channel node is a mapping node, and the predefined types include one or more of change case, custom, date/time, database query, new message, published, replace, standard, substring, table lookup, template, or web service.

12. The one or more computer storage media of claim 1, wherein the first channel node is a destination node, and the predefined types include one or more of a database destination, a discard destination, a file destination, an FTP destination, a socket destination, a web service destination, or an XMPP destination.

13. The one or more computer storage media of claim 1, wherein the one or more user interface controls includes a control which when selected displays the one or more automatically generated scripts in a scripting editor to allow the user to manually edit the one or more automatically generated scripts.

14. A computer system including one or more processors and one or more non-transitory computer storage media storing computer executable instructions which when executed by the one or more processors perform a method for graphically defining a channel for processing messages, the method comprising:

displaying, on a display device, a visual channel editor in which graphical representations of channel nodes can be arranged and interconnected to define a channel;

receiving user input to the visual channel editor that creates a plurality of graphical representations of channel nodes in the visual channel editor, the plurality of graphical representations including a graphical representation of a source node, zero or more graphical representations of a mapping node, zero or more graphical representations of a condition node, and at least one graphical representation of a destination node;

receiving user input that selects one of the plurality of graphical representations corresponding to a first channel node;

in response to the selection of the graphical representation, displaying, on the display device, a node configuration panel that displays one or more user interface controls that the user can manipulate to define configurable parameters for the first channel node, wherein the one or more user interface controls displayed in the node configuration panel include one or more fields that each list a number of predefined types for the first channel node that a user can select, and wherein the first channel node is a source node, and wherein the one or more fields include a source field and a format field, the source field for defining a source of messages to be processed in the channel, and the format field for defining a format for the messages;

receiving user input to the one or more user interface controls, the user input defining configurable parameters for the first channel node; and using the user input to the one or more user interface controls to automatically generate one or more scripts to implement functionality specified in the defined configurable parameters on messages that are processed by the first channel node.

15. The computer system of claim 14, wherein the computer system is one of a personal computer, a server, or a plurality of interconnected servers.

16. A method, performed by a computer system, for graphically defining a channel for converting a message in a first format used by a first HIT system into a second format used by a second HIT system, the method comprising:

displaying, on a display device, a visual channel editor in which graphical representations of channel nodes can be arranged and interconnected to define a channel for processing messages from a first HIT system to convert the messages from a first format used by the first HIT system into a second format used by a second HIT system;

receiving user input to the visual channel editor that creates a plurality of graphical representations of channel nodes in the visual channel editor, the plurality of graphical representations including a graphical representation of a source node, at least one graphical representation of a mapping node, and at least one graphical representation of a destination node;

receiving user input that selects each of the plurality of graphical representations;

in response to the selection of each of the graphical representation, displaying, on the display device, a node configuration panel that displays one or more user interface controls that the user can manipulate to define configurable parameters for the corresponding channel node;

receiving user input to the one or more user interface controls, the user input defining configurable parameters for the corresponding channel node; using the user input to the one or more user interface controls to automatically generate one or more scripts to implement functionality specified in the defined configurable parameters on messages that are processed by the corresponding channel node;

executing the channel, including executing the one or more scripts defined for the source node to receive messages in the first format from a specified source, executing the one or more scripts for each of the one or more mapping nodes to apply mapping functions to data of the messages to convert the messages to the second format, and executing the one or more scripts for each of the one or more destination nodes to store the messages in a specified location.

\* \* \* \* \*